United States Patent
Miller et al.

(10) Patent No.: US 9,757,428 B2
(45) Date of Patent: Sep. 12, 2017

(54) DESIGNED PEPTIDES FOR TIGHT JUNCTION BARRIER MODULATION

(71) Applicants: Benjamin L. Miller, Penfield, NY (US); Anna De Benedetto, Rochester, NY (US); Lisa A. Beck, Rochester, NY (US); Elizabeth A. Anderson, Rochester, NY (US)

(72) Inventors: Benjamin L. Miller, Penfield, NY (US); Anna De Benedetto, Rochester, NY (US); Lisa A. Beck, Rochester, NY (US); Elizabeth A. Anderson, Rochester, NY (US)

(73) Assignee: University of Rochester, Rochester, NY (US)

(*) Notice: Subject to any disclaimer, the term of this patent is extended or adjusted under 35 U.S.C. 154(b) by 0 days.

(21) Appl. No.: 14/912,098

(22) PCT Filed: Aug. 18, 2014

(86) PCT No.: PCT/US2014/051532
§ 371 (c)(1),
(2) Date: Feb. 15, 2016

(87) PCT Pub. No.: WO2015/024022
PCT Pub. Date: Feb. 19, 2015

(65) Prior Publication Data
US 2016/0199440 A1    Jul. 14, 2016

Related U.S. Application Data

(60) Provisional application No. 61/866,818, filed on Aug. 16, 2013.

(51) Int. Cl.
| | | |
|---|---|---|
| *A61K 38/00* | (2006.01) | |
| *A61K 38/17* | (2006.01) | |
| *A61K 39/12* | (2006.01) | |
| *A61K 9/00* | (2006.01) | |
| *A61K 38/44* | (2006.01) | |
| *A61K 39/145* | (2006.01) | |
| *C12N 7/00* | (2006.01) | |
| *A61K 39/39* | (2006.01) | |
| *A61K 39/00* | (2006.01) | |

(52) U.S. Cl.
CPC ............ *A61K 38/17* (2013.01); *A61K 9/0014* (2013.01); *A61K 9/0043* (2013.01); *A61K 38/44* (2013.01); *A61K 39/12* (2013.01); *A61K 39/145* (2013.01); *A61K 39/39* (2013.01); *C12N 7/00* (2013.01); *A61K 38/00* (2013.01); *A61K 2039/54* (2013.01); *A61K 2039/543* (2013.01); *A61K 2039/55516* (2013.01); *C12N 2760/16034* (2013.01); *C12N 2760/16071* (2013.01); *C12N 2760/16134* (2013.01); *C12Y 113/12007* (2013.01)

(58) Field of Classification Search
None
See application file for complete search history.

(56) References Cited

U.S. PATENT DOCUMENTS

| | | |
|---|---|---|
| 2004/0028613 A1 | 2/2004 | Quay et al. |
| 2009/0220435 A1 | 9/2009 | Quay et al. |
| 2013/0045267 A1 | 2/2013 | Beck et al. |
| 2013/0046257 A1* | 2/2013 | Beck ............... A61K 38/20 604/307 |
| 2016/0000777 A1 | 1/2016 | Beck et al. |

FOREIGN PATENT DOCUMENTS

| | | | |
|---|---|---|---|
| EP | 2561886 A1 | 2/2013 | |
| WO | WO 2011/097595 | * 8/2011 | |
| WO | 2013/026896 | 2/2013 | |

OTHER PUBLICATIONS

NCBI Reference Sequence NP-066924.1, downloaded online on Nov. 18, 2016.*
PCT International Search Report and Written Opinion corresponding to PCT/US2014/051532, mailed Mar. 25, 2015.
Mrsny et al., "A Key Claudin Extracellular Loop Domain is Critical for Epithelial Barrier Integrity," Am. J. Pathol. 172:905-915 (2008).
Zwanziger et al., "A Peptidomimetic Tight Junction Modulator to Improve Regional Analgesia," Mol. Pharmaceutics 9:1785-1794 (2012).
Zwanziger et al. "Claudin-Derived Peptides are Internalized via Specific Endocytosis Pathways," Annals N.Y. Acad. Sci. 1257:29-37 (2012).
Hackel, "Transient Opening of the Perineural Barrier for Analgesic Drug Delivery," PNAS109(29):E2018-2027 (2012).
Baumgartner et al., "A D-Peptide Analog of the Second Extracellular Loop of Claudin-3 and -4 Leads to Mis-Localized Claudin and Cellular Apoptosis in Mammary Epithelial Cells," Chem. Drug Biol. Des. 77:124-136 (2011).
Furuse et al., "Claudin-Based Tight Junctions are Crucial for the Mammalian Epidermal Barrier: A Lesson from Claudln-1-Deficient Mice," J. Cell Biol. 156:1099-1111 (2002).
De Benedetto et al., "Tight Junction Defects in Patients with Atopic Dermatitis," J. Allergy Clin. Immunol. 127:773-786 e7 (2010).
Karande et al., "Transcutaneous Immunization Using Common Chemicals," J. Controlled Rel. 138:134-140 (2009).
Rosenthal et al., "Analysis of Absorption Enhancers in Epithelial Cell Models," Annals N.Y. Acad. Sci. 1258:86-92 (2012).

(Continued)

*Primary Examiner* — James H Alstrum Acevedo
*Assistant Examiner* — Sergio Coffa
(74) *Attorney, Agent, or Firm* — LeClairRyan, a Professional Corporation

(57) ABSTRACT

According to aspects illustrated herein, there is provided an agent that transiently disrupts claudin-1 within tight junctions. The agent includes a peptide having at least 40% polar, uncharged amino acid residues and a self-assembled β-sheet secondary structure. According to aspects illustrated herein, there is also provided a transepithelial drug and vaccine formulations, as well as isolated peptides, pharmaceutical compositions, and transdermal delivery devices. Also described herein are methods of disrupting epithelial barrier and methods of administering the transepithelial formulations described herein.

19 Claims, 14 Drawing Sheets

(56) References Cited

OTHER PUBLICATIONS

Kondoh et al. "Spiral Progression in the Development of Absorption Enhancers Based on the Biology of Tight Junctions," Adv. Drug Delivery Rev. 64(6):515-522 (2011).
Hsu et al., "Elucidating the Signaling Mechanism of an Epithelial Tight-Junction Opening Induced by Chitosan," Biomat. 33:6254-6263 (2012).
Hsu et al., "Effects of pH on Molecular Mechanisms of Chitosan-Integrin Interactions and Resulting Tight-Junction Disruptions," Biomat. 34(3):784-793 (2012).
Choi et al., "Efficient Skin Permeation of Soluble Proteins via Flexible and Functional Nanocarrier," J. Controlled Rel. 157:272-278 (2011).
Lo et al,. "M Cell Targeting by a Claudin 4 Targeting Peptide Can Enhance Mucosal IgA Responses," BMC Biotechnology 12:7, 9 pages (2012).
Supplementary Partial European Search Report for corresponding European Patent Application No. 14836047.2, 9 pages (issued Feb. 28, 2017).
Extended European Search Report for corresponding European Patent Application No. 14836047.2, 15 pages (dated Jun. 6, 2017).

* cited by examiner

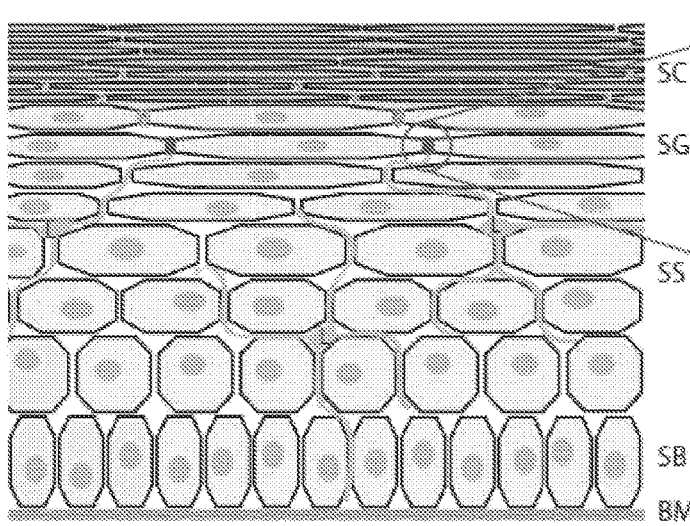
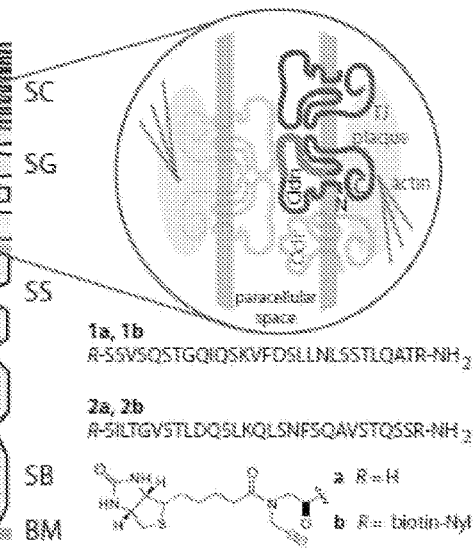

| SEQ ID NO: | Peptide | Polar uncharged | Gel behavior | Notes |
|---|---|---|---|---|
| | CLDN1 | | | |
| 5 | SSVSQSTGQIQSKVFDSLLNLSSTLQATR | 16/29 | Yes | EAA6-085A |
| 7 | GGMSCVSQSTGQIQCKV | | Yes | p. EAA5-053 |
| 8 | SCVSQSTGQIQCKV | | Yes | EAA4-083A |
| 9 | RRGSCVSQSGRR | | Yes | EAA5-013M |
| 12 | LWMSSVSQSTGQIQSKVFDS | 10/20 | | |
| 13 | MSSVSQSTGQIQSKVFDS | 10/18 | | CLDN1 52-69, C to S |
| 14 | MSSVSQSTGQIQSKV | 9/15 | | CLDN1 52-66, C to S |
| 15 | MSSVSQST | 6/8 | | CLDN1 52-59, C to S |
| | Scrambled | | | |
| 6 | SILTGVSTLDQSLKQLSNFSQAVSTQSSR | 16/29 | Yes | EAA6-061B |
| 10 | ISGVQCCQTKQSS | 9/13 | Yes | EAA5-013Jscr |
| 11 | RRGVCSSSQGRR | 5/12 (5/6, core) | Yes | EAA5-013Mscr |
| 16 | ISMSQQVSQSGVSDKFST | 10/18 | | scrCLDN1 52-69, C to S |
| 17 | SIMSGKQSSVQSQVT | 9/15 | | scrCLDN1 52-66, C to S based on EAA5-013Fscr |
| 18 | VSMSSTSQ | 6/8 | | scrCLDN1 52-59, C to S |
| 19 | VSSSSQ | 5/6 | | based on EAA5-013Mscr |
| 20 | SILTGVST | 4/8 | | based on AMYLPRED2 |

*FIG. 1C*

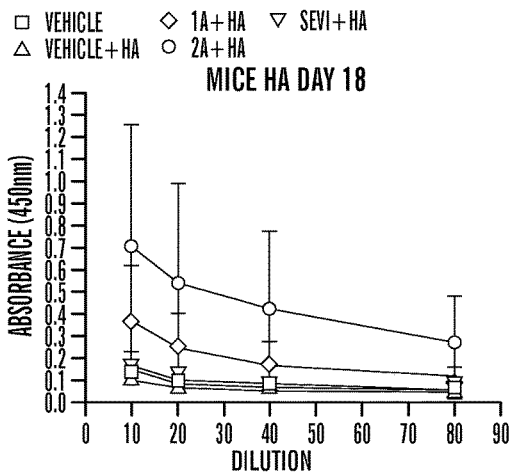
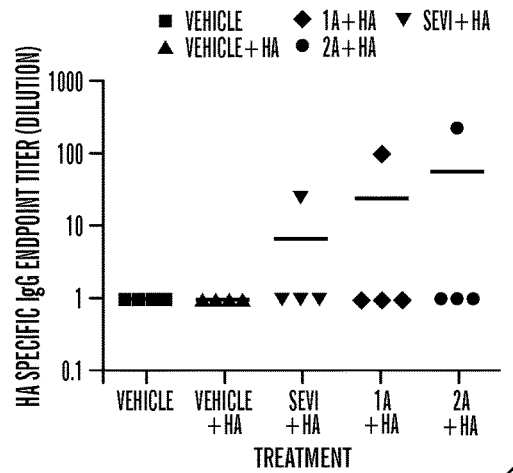
FIG. 12A
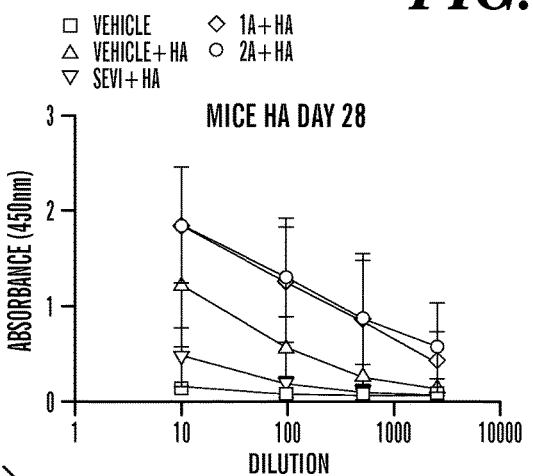
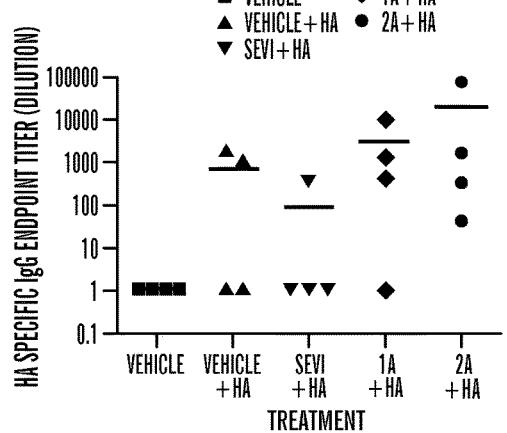
FIG. 12B
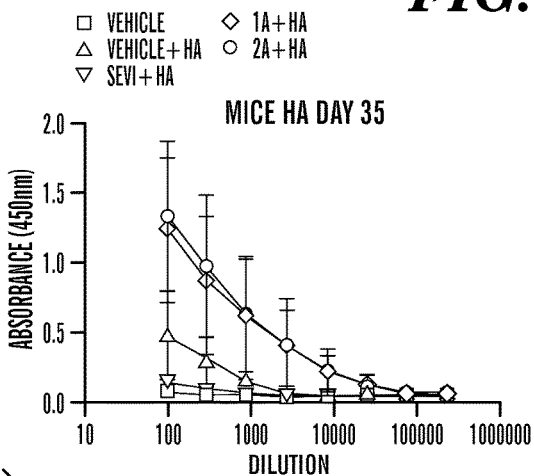
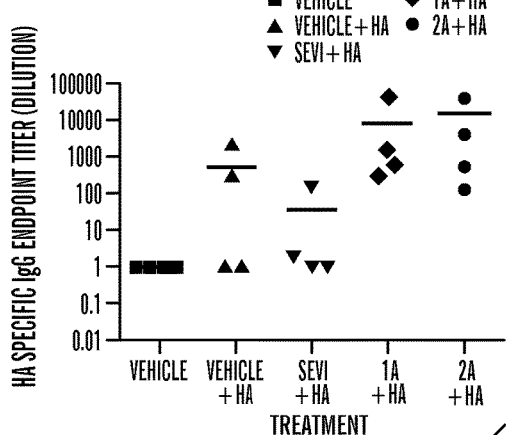
FIG. 12C

```
                         SEQUENCE LISTING

<160> NUMBER OF SEQ ID NOS: 31

<210> SEQ ID NO 1
<211> LENGTH: 29
<212> TYPE: PRT
<213> ORGANISM: Artificial
<220> FEATURE:
<223> OTHER INFORMATION: Rat Cldn-1-Derived Peptide

<400> SEQUENCE: 1

Ser Ser Val Ser Gln Ser Thr Gly Gln Ile Gln Ser Lys Val Phe Asp
1               5                   10                  15

Ser Leu Leu Asn Leu Asn Ser Thr Leu Gln Ala Thr Arg
            20                  25

<210> SEQ ID NO 2
<211> LENGTH: 28
<212> TYPE: PRT
<213> ORGANISM: Rattus norvegicus

<400> SEQUENCE: 2

Ser Cys Val Ser Gln Ser Thr Gly Gln Ile Gln Cys Lys Val Phe Asp
1               5                   10                  15

Ser Leu Leu Asn Leu Asn Ser Thr Leu Gln Ala Thr
            20                  25

<210> SEQ ID NO 3
<211> LENGTH: 28
<212> TYPE: PRT
<213> ORGANISM: Artificial
<220> FEATURE:
<223> OTHER INFORMATION: Human Cldn-1-Derived Peptide

<400> SEQUENCE: 3

Ser Ser Val Ser Gln Ser Thr Gly Gln Ile Gln Ser Lys Val Phe Asp
1               5                   10                  15

Ser Leu Leu Asn Leu Ser Ser Thr Leu Gln Ala Thr
            20                  25

<210> SEQ ID NO 4
<211> LENGTH: 28
<212> TYPE: PRT
<213> ORGANISM: Artificial
<220> FEATURE:
<223> OTHER INFORMATION: Human Cldn-1-Derived Peptide
<220> FEATURE:
<221> NAME/KEY: misc_feature
```

```
<222> LOCATION: (10)..(10)
<223> OTHER INFORMATION: Xaa can be any naturally occurring amino acid

<400> SEQUENCE: 4

Ser Cys Val Ser Gln Ser Thr Gly Gln Xaa Gln Cys Lys Val Phe Asp
1               5                   10                  15

Ser Leu Leu Asn Leu Ser Ser Thr Leu Gln Ala Thr
            20                  25

<210> SEQ ID NO 5
<211> LENGTH: 29
<212> TYPE: PRT
<213> ORGANISM: Artificial
<220> FEATURE:
<223> OTHER INFORMATION: Peptide for Tight Junction Barrier Modulation

<400> SEQUENCE: 5

Ser Ser Val Ser Gln Ser Thr Gly Gln Ile Gln Ser Lys Val Phe Asp
1               5                   10                  15

Ser Leu Leu Asn Leu Ser Ser Thr Leu Gln Ala Thr Arg
            20                  25

<210>

-continued

<400> SEQUENCE: 9

Arg Arg Gly Ser Cys Val Ser Gln Ser Gly Arg Arg
1 5 10

<210> SEQ ID NO 10
<211> LENGTH: 13
<212> TYPE: PRT
<213> ORGANISM: Artificial
<220> FEATURE:
<223> OTHER INFORMATION: Peptide for Tight Junction Barrier Modulation

<400> SEQUENCE: 10

Ile Ser Gly Val Gln Cys Cys Gln Thr Lys Gln Ser Ser
1 5 10

<210> SEQ ID NO 11
<211> LENGTH: 12
<212> TYPE: PRT
<213> ORGANISM: Artificial
<220> FEATURE:
<223> OTHER INFORMATION: Peptide for Tight Junction Barrier Modulation

<400> SEQUENCE: 11

Arg Arg Gly Val Cys Ser Ser Ser Gln Gly Arg Arg
1 5 10

<210> SEQ ID NO 12
<211> LENGTH: 20
<212> TYPE: PRT
<213> ORGANISM: Artificial
<220> FEATURE:
<223> OTHER INFORMATION: Peptide for Tight Junction Barrier Modulation

<400> SEQUENCE: 12

Leu Trp Met Ser Ser Val Ser Gln Ser Thr Gly Gln Ile Gln Ser Lys
1 5 10 15

Val Phe Asp Ser
20

<210> SEQ ID NO 13
<211> LENGTH: 18
<212> TYPE: PRT
<213> ORGANISM: Artificial
<220> FEATURE:
<223> OTHER INFORMATION: Peptide for Tight Junction Barrier Modulation

<400> SEQUENCE: 13

Met Ser Ser Val Ser Gln Ser Thr Gly Gln Ile Gln Ser Lys Val Phe
1 5 10 15

Asp Ser

<210> SEQ ID NO 14
<211> LENGTH: 15
<212> TYPE: PRT
<213> ORGANISM: Artificial
<220> FEATURE:
<223> OTHER INFORMATION: Peptide for Tight Junction Barrier Modulation

<400> SEQUENCE: 14

Met Ser Ser Val Ser Gln Ser Thr Gly Gln Ile Gln Ser Lys Val
1 5 10 15

<210> SEQ ID NO 15
<211> LENGTH: 8
<212> TYPE: PRT

```
<213> ORGANISM: Artificial
<220> FEATURE:
<223> OTHER INFORMATION: Peptide for Tight Junction Barrier Modulation

<400> SEQUENCE: 15

Met Ser Ser Val Ser Gln Ser Thr
1               5

<210> SEQ ID NO 16
<211> LENGTH: 18
<212> TYPE: PRT
<213> ORGANISM: Artificial
<220> FEATURE:
<223> OTHER INFORMATION: Peptide for Tight Junction Barrier Modulation

<400> SEQUENCE: 16

Ile Ser Met Ser Gln Gln Val Ser Gln Ser Gly Val Ser Asp Lys Phe
1               5                   10                  15

Ser Thr

<210> SEQ ID NO 17
<211> LENGTH: 15
<212> TYPE: PRT
<213> ORGANISM: Artificial
<220> FEATURE:
<223> OTHER INFORMATION: Peptide for Tight Junction Barrier Modulation

<400> SEQUENCE: 17

Ser Ile Met Ser Gly Lys Gln Ser Ser Val Gln Ser Gln Val Thr
1               5                   10                  15

<210> SEQ ID NO 18
<211> LENGTH: 8
<212> TYPE: PRT
<213> ORGANISM: Artificial
<220> FEATURE:
<223> OTHER INFORMATION: Peptide for Tight Junction Barrier Modulation

<400> SEQUENCE: 18

Val Ser Met Ser Ser Thr Ser Gln
1               5

<210> SEQ ID NO 19
<211> LENGTH: 6
<212> TYPE: PRT
<213> ORGANISM: Artificial
<220> FEATURE:
<223> OTHER INFORMATION: Peptide for Tight Junction Barrier Modulation

<400> SEQUENCE: 19

Val Ser Ser Ser Ser Gln
1               5

<210> SEQ ID NO 20
<211> LENGTH: 8
<212> TYPE: PRT
<213> ORGANISM: Artificial
<220> FEATURE:
<223> OTHER INFORMATION: Peptide for Tight Junction Barrier Modulation

<400> SEQUENCE: 20

Ser Ile Leu Thr Gly Val Ser Thr
1               5

<210> SEQ ID NO 21
<211> LENGTH: 8
```

```
<212> TYPE: PRT
<213> ORGANISM: Artificial
<220> FEATURE:
<223> OTHER INFORMATION: Peptide for Tight Junction Barrier Modulation

<400> SEQUENCE: 21

Ser Ser Val Ser Gln Ser Thr Gly
1               5

<210> SEQ ID NO 22
<211> LENGTH: 8
<212> TYPE: PRT
<213> ORGANISM: Artificial
<220> FEATURE:
<223> OTHER INFORMATION: Peptide for Tight Junction Barrier Modulation

<400> SEQUENCE: 22

Gly Gln Ile Gln Ser Lys Val Gly
1               5

<210> SEQ ID NO 23
<211> LENGTH: 9
<212> TYPE: PRT
<213> ORGANISM: Artificial
<220> FEATURE:
<223> OTHER INFORMATION: Peptide for Tight Junction Barrier Modulation

<400> SEQUENCE: 23

Leu Asn Leu Ser Ser Thr Leu Gln Gly
1               5

<210> SEQ ID NO 24
<211> LENGTH: 8
<212> TYPE: PRT
<213> ORGANISM: Artificial
<220> FEATURE:
<223> OTHER INFORMATION: Peptide for Tight Junction Barrier Modulation

<400> SEQUENCE: 24

Asn Ser Val Val Gln Ser Thr Gly
1               5

<210> SEQ ID NO 25
<211> LENGTH: 8
<212> TYPE: PRT
<213> ORGANISM: Artificial
<220> FEATURE:
<223> OTHER INFORMATION: Peptide for Tight Junction Barrier Modulation

<400> SEQUENCE: 25

Gly Gln Met Gln Ser Lys Val Gly
1               5

<210> SEQ ID NO 26
<211> LENGTH: 29
<212> TYPE: PRT
<213> ORGANISM: Artificial
<220> FEATURE:
<223> OTHER INFORMATION: Peptide for Tight Junction Barrier Modulation

<400> SEQUENCE: 26

Ser Cys Val Ser Gln Ser Thr Gly Gln Ile Gln Cys Lys Val Phe Asp
1               5                   10                  15

Ser Leu Leu Asn Leu Ser Ser Thr Leu Gln

-continued

```
<210> SEQ ID NO 27
<211> LENGTH: 30
<212> TYPE: PRT
<213> ORGANISM: Artificial
<220> FEATURE:
<223> OTHER INFORMATION: Peptide for Tight Junction Barrier Modulation

<400> SEQUENCE: 27

Met Ser Cys Val Ser Gln Ser Thr Gly Gln Ile Gln Cys Lys Val Phe
1               5                   10                  15

Asp Ser Leu Leu Asn Leu Ser Ser Thr Leu Gln Ala Thr Arg
            20                  25                  30

<210> SEQ ID NO 28
<211> LENGTH: 17
<212> TYPE: PRT
<213> ORGANISM: Artificial
<220> FEATURE:
<223> OTHER INFORMATION: Peptide for Tight Junction Barrier Modulation

<400> SEQUENCE: 28

Gly Gly Gly Met Ser Cys Val Ser Gln Ser Thr Gly Gln Ile Gln Cys
1               5                   10                  15

Lys

<210> SEQ ID NO 29
<211> LENGTH: 8
<212> TYPE: PRT
<213> ORGANISM: Artificial
<220> FEATURE:
<223> OTHER INFORMATION: Peptide for Tight Junction Barrier Modulation

<400> SEQUENCE: 29

Gly Gly Ser Cys Val Ser Gln Ser
1               5

<210> SEQ ID NO 30
<211> LENGTH: 19
<212> TYPE: PRT
<213> ORGANISM: Artificial
<220> FEATURE:
<223> OTHER INFORMATION: Peptide for Tight Junction Barrier Modulation

<400> SEQUENCE: 30

Arg Arg Gly Ser Cys Val Ser Gln Ser Thr Gly Gln Ile Gln Cys Lys
1               5                   10                  15

Gly Arg Arg

<210> SEQ ID NO 31
<211> LENGTH: 19
<212> TYPE: PRT
<213> ORGANISM: Artificial
<220> FEATURE:
<223> OTHER INFORMATION: Peptide for Tight Junction Barrier Modulation

<400> SEQUENCE: 31

Arg Arg Gly Ile Ser Gly Val Gln Cys Cys Gln Thr Lys Gln Ser Ser
1               5                   10                  15

Gly Arg Arg
```

DESIGNED PEPTIDES FOR TIGHT JUNCTION BARRIER MODULATION

This application is a national stage application under 35 U.S.C. §371 of PCT Application No. PCT/US2014/051532, filed Aug. 18, 2014, which claims the benefit of U.S. Provisional Patent Application Ser. No. 61/866,818, filed Aug. 16, 2013, the disclosure of which is incorporated herein by reference in its entirety.

This invention was made with support from the National Institutes of Health under grant number 5 T32 AR007472-25. The U.S. government has certain rights in this invention.

TECHNOLOGICAL FIELD

Disclosed herein are isolated peptides suitable for disrupting an epithelial barrier, transepithelial drug or vaccine formulations, drug delivery vehicles for delivering these formulations, and methods of using of these formulations for disrupting an epithelial barrier.

BACKGROUND

Intact epithelial barrier (e.g., skin) is important for health, functioning to exclude exogenous chemicals, antigens, and pathogens from the body (De Benedetto et al., "Skin Barrier Disruption: A Requirement for Allergen Sensitization?," *J. Invest. Dermatol.* 132:949-963 (2012); O'Neill et al., "Tight Junction Proteins and the Epidermis," *Exp. Dermatol.* 20:88-91 (2011); Kubo et al., "Epidermal Barrier Dysfunction and Cutaneous Sensitization in Atopic Diseases," *J. Clin. Invest.* 122:440-447 (2012)). As such, it impedes transdermal delivery of therapeutic agents and vaccines. To address this issue, there has been a sustained and extensive effort to develop cell-penetrating peptides to facilitate transdermal delivery (Milletti, "Cell-Penetrating Peptides: Classes, Origin, and Current Landscape," *Drug Discov. Today* 17:850-860 (2012); Stanzl et al., "Fifteen Years of Cell-Penetrating, Guanidinium-Rich Molecular Transporters: Basic Science, Research Tools, and Clinical Applications," *Acc. Chem. Res.* 46(12):2944-54 (2013)). While this effort has produced many notable successes, an alternative strategy is to reversibly weaken the interactions between cells, thereby enabling paracellular delivery without the use of cell penetrating peptides.

The paracellular barrier in epithelial cell layers is sealed via tight junctions ("TJs"). In the skin, TJs form in the stratum granulosum ("SG") (Yoshida et al., "Functional Tight Junction Barrier Localizes in the Second Layer of the Stratum Granulosum of Human Epidermis," *J. Dermatol. Sci.* 71(2):89-99 (2013)) and may even persist into the stratum corneum ("SC") (Haftek et al., "Compartmentalization of the Human Stratum Corneum by Persistent Tight Junction-Like Structures," *Exp. Dermatol.* 20:617-621 (2011); Sugawara et al., "Tight Junction Dysfunction in the Stratum Granulosum Leads to Aberrant Stratum Corneum Barrier Function in Claudin-1-Deficient Mice," *J. Dermatol. Sci.* 70(1):12-18 (2013)). TJs and the SC act in concert to form the epidermal barrier.

TJs form strands of protein assemblies in an equatorial belt around epithelial cells. Claudins bridge the actin cytoskeleton on the cytoplasmic face (through zona occludens proteins in the TJ plaque), span the plasma membrane, and interact with claudins on neighboring cells. At least 23 mammalian claudins have been identified thus far (Van Itallie et al., "Claudin Interactions In and Out of the Tight Junction," *Tissue Barriers* 1(3): e25247 (2013)). Claudins are tetraspannins, with two extracellular loops and a long cytoplasmic C-terminal domain. At the cell surface, claudins form dimers through their extracellular domains that assemble with those on the opposing cell membrane, forming strands embedded in both cell membranes (Kaufmann et al., "Visualization and Quantitative Analysis of Reconstituted Tight Junctions Using Localization Microscopy," *PLoS ONE* 7:e31128 (2012)). The number and character of these strands determines the strength of the paracellular barrier. Differential expression of claudin family members tailors the permeability characteristics for each tissue barrier (gut v. skin v. blood-brain barrier) (Anderson et al., "Physiology and Function of the Tight Junction," *Cold Spring Harb Perspect Biol.* 1(2):a002584-a002584 (2009)). Several other membrane proteins including occludin ("Ocln"), tricellulin, and JAM-A also participate in the TJ complex and contribute to barrier function and regulation (Kirschner et al., "Contribution of Tight Junction Proteins to Ion, Macromolecule, and Water Barrier in Keratinocytes," *J. Invest. Dermatol.* 133:1161-1169 (2013); Cording et al., "In Tight Junctions, Claudins Regulate the Interactions Between Occludin, Tricellulin and Marveld3, Which, Inversely, Modulate Claudin Oligomerization," *J. Cell Sci.* 126:554-564 (2013)).

Claudin 1 ("Cldn1") is highly expressed in lung epithelium, epidermal keratinocytes, and dendritic cells that populate the epidermis (Kast et al., "The Broad Spectrum of Interepithelial Junctions in Skin and Lung," *J. Allergy Clin. Immunol.* 130:544-546 (2012); Kubo et al., "External Antigen Uptake by Langerhans Cells With Reorganization of Epidermal Tight Junction Barriers," *J. Exper. Med.* 206:2937-2946 (2009)). Increasing Cldn1 expression in vitro enhances the paracellular permeability barrier (Pfeiffer et al., "Claudin-1 Induced Sealing of Blood—Brain Barrier Tight Junctions Ameliorates Chronic Experimental Autoimmune Encephalomyelitis," *Acta Neuropathol.* 122:601-614 (2011); Inai et al., "Claudin-1 Contributes to the Epithelial Barrier Function in MDCK Cells," *European J. Cell Biol.* 78:1-7 (1999)). In humans, a heritable Cldn1 deficiency has been reported in neonatal ichthyosis-hypotrichosis-sclerosing cholangitis syndrome, which results in severe ichthyosis and neonatal cholestasis (Hadj-Rabia et al., "Claudin-1 Gene Mutations in Neonatal Sclerosing Cholangitis Associated With Ichthyosis: A Tight Junction Disease," *Gastroenterology* 127:1386-1390 (2004)). Mice lacking Cldn1 die of dehydration within one day of birth, indicating that the protein is essential for skin barrier (Yoshida et al., "Functional Tight Junction Barrier Localizes in the Second Layer of the Stratum Granulosum of Human Epidermis," *J. Dermatol. Sci.* 71(2):89-99 (2013); Furuse et al., "Claudin-Based Tight Junctions are Crucial for the Mammalian Epidermal Barrier: A Lesson From Claudin-1-Deficient Mice," *J. Cell Biol.* 156:1099-1111 (2002)). Similarly, patients with atopic dermatitis ("AD") have greater transepidermal water loss and paracellular permeability in their nonlesional skin, and also have markedly reduced Cldn1 expression (De Benedetti, "Tight Junction Defects in Patients With Atopic Dermatitis," *J. Allergy Clint. Immune.* 127:773-786.e7 (2010)).

Synthetic peptides derived from the sequence of the extracellular loops of TJ proteins (claudins and Ocln) have been shown to disrupt barrier function at high concentration by several research groups (Wong et al., "A Synthetic Peptide Corresponding to the Extracellular Domain of Occludin Perturbs the Tight Junction Permeability Barrier," *J. Cell Biol.* 136:399-409 (1997); Mrsny et al., "A Key Claudin Extracellular Loop Domain Is Critical for Epithelial Barrier Integrity," *Am. J. Path.* 172:905-915 (2008); Baumgartner et al., "A d-Peptide Analog of the Second Extracellular Loop of Claudin-3 and -4 Leads to Mislocalized Claudin and Cellular Apoptosis in Mammary Epithelial Cells," *Chem. Biol. & Drug Des.* 77:124-136 (2011); Zwanziger et al., "A Peptidomimetic Tight Junction Modulator to Improve Regional Analgesia," *Mol. Pharm.* 9:1785-1794 (2012)). A peptide from the second extracellular loop of claudins 3 and 4 induces mislocalization of occludin and apoptosis (Baumgartner et al., "A d-Peptide Analog of the Second Extracellular Loop of Claudin-3 and -4 Leads to Mislocalized Claudin and Cellular Apoptosis in Mammary Epithelial Cells," *Chem. Biol. & Drug Des.* 77:124-136 (2011); Beeman et al., "Occluding Is Required for Apoptosis When Claudin—Claudin Interactions are Disrupted," *Cell Death Dis.* 3:e273 (2012)). In T84 (transplantable human carcinoma) cells, application of 25 μM of the rat Cldn1 (53-80) peptide was shown to inhibit calcium-induced TJ formation, and 200 μM was able to disrupt intact TJs (Mrsny et al., "A Key Claudin Extracellular Loop Domain Is Critical for Epithelial Barrier Integrity," *Am. J. Path.* 172:905-915 (2008)). Cysteines were not required for TJ disruption. Rat Cldn1 (53-81, C54,64S) peptide disrupted Caco-2, HEK-293, and rat perineural TJ barriers in vivo at 200-300 μM (Zwanziger et al., "A Peptidomimetic Tight Junction Modulator to Improve Regional Analgesia," *Mol. Pharm.* 9:1785-1794 (2012)). Zwanziger, et al. noted that this peptide has β-sheet structure when solubilized with SDS as evidenced by circular dichroism. Rat Cldn1 (53-81, C54,64S) peptide co-localizes with Cldn1 and is internalized by subconfluent HEK-293 cells (Zwanziger et al., "Claudin-Derived Peptides are Internalized Via Specific Endocytosis Pathways," *Ann. NY Acad. Sci.* 1257:29-37 (2012)).

A relatively high concentration of tested peptides was required to induce alteration in TJ appearance and increase paracellular permeability in these prior studies. No claudin-derived peptides capable of disrupting TJs at low or sub micromolar concentrations have been identified previously. Other than knowledge of the claudin-1 second loop domain and its amino acid sequence, structural features responsible for disruption have not been identified to date.

Further, transepithelial (including transdermal) delivery of large and/or hydrophilic therapeutics or antigens is not straightforward due to, e.g., the dual barrier functions of skin and mucosa. A small subset of small molecule drugs can readily cross epithelial cell barriers via transcellular transport by virtue of their small size and hydrophobicity. Larger or more hydrophilic molecules do not spontaneously cross cellular membranes and are excluded by paracellular tight junction barriers. Reversible, controlled barrier disruption that would enable noninvasive delivery of drugs and needle-free vaccines is particularly desirable for peptide/protein based therapeutics or antigens that do not readily cross cellular membranes.

Disclosed herein are peptides and formulations directed to overcoming these and other limitations in the art.

SUMMARY

According to aspects illustrated herein, there is provided an agent that transiently disrupts claudin-1 within tight junctions. The agent includes a peptide having at least 40% polar, uncharged amino acid residues and a self-assembled β-sheet secondary structure.

According to further aspects illustrated herein, there is provided an agent that transiently disrupts claudin-1 within tight junctions. The agent includes a peptide having at least 40% polar, uncharged amino acid residues and a self-assembled β-sheet secondary structure. The peptide does not consist of the amino acid sequence of SSVSQSTGQIQSKVFDSLLNLNSTLQATR (SEQ ID NO:1), SCVSQSTGQIQCKVFDSLLNLNSTLQAT (SEQ ID NO:2), SSVSQSTGQIQSKVFDSLLNLSSTLQAT (SEQ ID NO:3), or SCVSQSTGQ[I/V]QCKVFDSLLNLSSTLQAT (SEQ ID NO:4).

According to further aspects illustrated herein, there is provided a transepithelial drug formulation. The transepithelial drug formulation includes a pharmaceutically suitable carrier; an effective amount of a therapeutic agent; and an agent that transiently disrupts claudin-1 within tight junctions as described herein.

According to further aspects illustrated herein, there is provided a transepithelial vaccine formulation. The transepithelial vaccine formulation includes a pharmaceutically suitable carrier; an effective amount of an antigen or antigen-encoding nucleic acid molecule present in the carrier, and optionally one or more adjuvants; and an agent that transiently disrupts claudin-1 within tight junctions as described herein.

According to further aspects illustrated herein, there is provided an isolated peptide including the amino acid sequence of SSVSQSTGQIQSKVFDSLLNLSSTLQATR (SEQ ID NO: 5), SILTGVSTLDQSLKQLSNFSQAVSTQSSR (SEQ ID NO:6), GGMSCVSQSTGQIQCKV (SEQ ID NO:7), SCVSQSTGQIQCKV (SEQ ID NO:8), RRGSCVSQSGRR (SEQ ID NO: 9), ISGVQCCQTKQSS (SEQ ID NO: 10), RRGVCSSSQGRR (SEQ ID NO:11), LWMSSVSQSTGQIQSKVFDS (SEQ ID NO:12), MSSVSQSTGQIQSKVFDS (SEQ ID NO:13), MSSVSQSTGQIQSKV (SEQ ID NO:14), MSSVSQST (SEQ ID NO:15), ISMSQQVSQSGVSDKFST (SEQ ID NO:16), SIMSGKQSSVQSQVT (SEQ ID NO:17), VSMSSTSQ (SEQ ID NO:18), VSSSSQ (SEQ ID NO:19), SILTGVST (SEQ ID NO:20), SSVSQSTG (SEQ ID NO:21), GQIQSKVG (SEQ ID NO:22), LNLSSTLQG (SEQ ID NO:23), NSVVQSTG (SEQ ID NO:24), GQMQSKVG (SEQ ID NO:25), or SCVSQSTGQIQCKVFDSLLNLSSTLQATR (SEQ ID NO:26).

According to further aspects illustrated herein, there is provided a pharmaceutical composition including an isolated peptide as described herein and a pharmaceutically suitable carrier.

According to further aspects illustrated herein, there is provided a transdermal patch including (i) an agent that transiently disrupts claudin-1 within tight junctions as described herein, (ii) a transepithelial drug formulation as described herein, or (iii) a transepithelial vaccine formulation as described herein.

According to further aspects illustrated herein, there is provided a method of disrupting an epithelial barrier. The method includes applying to an epithelial site an amount of an agent that transiently disrupts claudin-1 within tight junctions as described herein, where the applying is effective to disrupt claudin-1 in epithelial cells present at the site and thereby disrupt barrier formation at the epithelial site.

According to further aspects illustrated herein, there is provided a method of administering a transepithelial drug formulation to a subject. The method includes applying the transepithelial drug formulation as described herein to an epithelial site on the subject.

According to further aspects illustrated herein, there is provided a method of administering a transepithelial vaccine formulation to a subject. The method includes applying the transepithelial vaccine formulation as described herein to an epithelial site on the subject.

Aspects illustrated herein utilize peptides with defined physiochemical properties to reversibly disrupt TJ function, which controls paracellular diffusion in epithelial cells. These peptides represent a new class of nonpathogenic, functional amyloid. As described herein, the structure of TJ-disrupting peptides and their mechanism of action was examined by studying the biological and biophysical characteristics of the homologous human peptide hCldn1 (53-81, C54,64S) (SEQ ID NO:5) (referred to herein as "Peptide 1a"). It was found that, when solubilized in the presence of surfactant, Peptide 1a disrupts TJs in cultured cells at a concentration two orders of magnitude lower than previously reported for Cldn1 peptides (Mrsny et al., "A Key Claudin Extracellular Loop Domain Is Critical for Epithelial Barrier Integrity," *Am. J. Path.* 172:905-915 (2008); Zwanziger et al., "A Peptidomimetic Tight Junction Modulator to Improve Regional Analgesia," *Mol. Pharm.* 9:1785-1794 (2012), which are hereby incorporated by reference in their entirety). Biophysical characterization indicates that Peptide 1a can form amyloid-like fibrils rich in β-sheet secondary structure. As described herein, a previously unknown scrambled peptide with identical amino acid content, hydrophobicity and pI, but random sequence (designated as Peptide 2a), also adopts a β-sheet conformation, forms fibrils, and disrupts TJ.

As shown in the Examples, infra, Cldn1-based peptides were synthesized and their structural and biophysical properties, as well as their ability to alter TJs, were analyzed. Using a human bronchial epithelial cell line (16HBE), claudin peptide and its scrambled analog were synthesized, both of which disrupt TJs in a dose-dependent manner at concentrations an order of magnitude lower than what has been reported with other Cldn1 peptides. Peptide exposure also disrupts paracellular barrier function, allowing diffusion of molecules that range in size and scope from fluorescein to a therapeutic antibody, with no evidence of cytotoxicity. Transepithelial electrical resistance ("TER") recovers after removal of the peptides. Peptide exposure alters Cldn1 and occludin expression patterns, as observed by immunofluorescence staining. When solubilized in surfactant, both a Cldn1 peptide and its corresponding scrambled analog spontaneously formed fibrils. Circular dichroism and Fourier transform infrared spectroscopy demonstrate that these fibrils are rich in β-sheet secondary structure, and X-ray powder diffraction is consistent with cross-β structures. These fibrils bound Thioflavin T, a dye considered diagnostic for amyloid. The observation that the scrambled peptide functions at least as well as the Cldn1 sequence in barrier disruption, as well as adopting a similar conformation, indicates the existence of an entirely new class of amyloid-forming peptides, and uncovers a new strategy for enhancing the transepithelial delivery of therapeutic molecules.

BRIEF DESCRIPTION OF THE DRAWINGS

FIGS. 1A-1C are a schematic illustrations of TJ in the epidermis, as well as Claudin-1, peptide 1, and peptide 2 (which are described in more detail below) (FIGS. 1A and 1B), as well as a table of other peptides showing evidence of self-assembly (FIG. 1C). Schematics of TJ in the epidermis, Cldn1 in the TJ, and peptides used in the experiments described herein are shown in FIGS. 1A-1B. FIG. 1B is a magnified schematic showing epidermal TJs form a paracellular barrier between keratinocytes in the SG. The SC and TJs act in concert to form the skin barrier; L, Langerhans cell; SS, stratum spinosum; SB, stratum basale; BM, basement membrane. Cldn1 self-assembles and interacts with other TJ proteins primarily through its first extracellular loop in the paracellular space. The C-terminus of Cldn1 is anchored to the actin cytoskeleton through the cytoplasmic TJ plaque proteins. Peptide 1 represents half of the first extracellular loop of human Cldn1, with its Cys residues mutated to Ser (hCldn1 (53-81, C54,64S)) (SEQ ID NO:5). Peptide 2 is a scrambled sequence (SEQ ID NO:6). R=H or biotin-N-propargyl glycine. Additional exemplary peptides that have shown evidence of self-assembly and are useful in accordance with embodiments illustrated herein are found in FIG. 1C.

FIG. 3C shows experimental results in which, after 24 hours exposure, paracellular diffusion of sodium fluorescein or FITC-dextran (FD-40) to the basolateral media was determined after 30 minutes (n=4). Surfactant concentrations were kept constant in the absence (vehicle) and presence of the peptide. Error bars represent the standard error of the mean ("SEM"); * indicates statistical significance relative to vehicle (P<0.05, two-tailed T-test); and ND stands for no data available. FIG. 3D shows a bar graph of experimental results demonstrating that application of peptide 1a (Cldn1 peptide) and 2a (Scrambled peptide) facilitate diffusion of a therapeutic monoclonal antibody (168 kD). After 24 hours exposure to vehicle or peptide (consistent surfactant concentration), fluorescently labeled Synagis mAb was applied apically and diffusion to the basolateral media was determined after 30 minutes or 18 hours (n=4). Error bars represent SEM, and * indicates statistical significance relative to vehicle (P<0.05, two-tailed T-test). FIG. 3E shows FITC-dextran permeability after 18 hours of diffusion for peptides 1a and 2a. Fluorescein Dextran (40 kD) in PBS was added to the apical media after 24 h exposure to Cldn1 peptide 1a or Scrambled peptide 2a (600 μg/mL FD-40 final apical concentration). Basolateral media was collected after 18 hours incubation, and fluorescence normalized to the positive control (cells lysed with 1% Triton-X100).

FIG. 4B shows fluorescein permeability for labeled peptides 1b and 2b.

FIGS. 5A-5B are bar graphs of results showing that TJ function recovers in 16HBE cultures after removal of peptides. No alterations in WST1 metabolism were observed with 1, 4, 12 (representative experiment shown in FIG. 5A) or 24 hour exposure to peptides 1a and 2a. (U, untreated media; V, vehicle; L, lysed cells; 1a (Cldn1, center section of graph, 0.024-12 µM); or 2a (Scrambled, right section of graph, 0.024 to 12 µM)). FIG. 5B shows results demonstrating that barrier function recovers after peptides 1a (left section of graph, 0.024 to 12 µM) or 2a (right section of graph 0.024 to 12 µM) were removed; light bars indicate mean TER values after peptide exposure, while dark bars indicate mean TER values after peptide washout and a further 24 h incubation. Grey horizontal lines indicate the mean TER values for vehicle. Error bars represent the SEM (n=4). FIG. 5C shows results relating to the study of cytotoxic oligomers by WST1 assay (taken from 130908RM). Peptide stocks were diluted into warm media and added directly to cells without incubation. After 12 h exposure, WST1 reagent was added and cellular metabolic activity was assessed colorimetrically. Amyloid oligomers are transient folding intermediates that can cause toxicity through membrane disruption, whereas fibrils are thermodynamically stable. As was expected, cytotoxicity was observed after incubation of cells with low concentrations of freshly diluted 1a (1.2 µM) and 2a (200 nM) that had sufficient opportunity to equilibrate. (Dark bars indicate peptide 1a, light bars peptide 2a.)

FIGS. 6A and 6E, untreated media; FIGS. 6B and 6F, vehicle control containing 0.006% Pluronic® F-127 and 0.03% DMSO; 7C and 7G, 2.4 µM 1b; or 7D and 7H, 2.4 µM 2b. Scale bar=25 µm.

FIG. 8D show results of a CD experiment. CD of labeled peptides 1b and 2b (1 µM). Peptides were diluted into phosphate buffer 48 hours prior to spectra being taken (in a 1 cm path length cuvette). FIG. 8E includes graphs showing FTIR spectra of labeled peptides 1b and 2b.

As shown in FIGS. 11A-11F, application of peptide 1A resulted in a trend of higher amounts of luciferase lost from the nasal cavity, consistent with a peptide-mediated increase in permeability.

FIGS. 12A-12E are graphs showing experimental results of immunization experiments with influenza hemagglutinin. Mice (4 mice per group) were treated in the nasal cavity with vehicle alone (0.006% Pluronic F127 in saline), vehicle plus influenza hemagglutinin (HA), or vehicle plus HA plus a permeabilizing agent (peptides 1A or 2A, or semen-derived enhancer of virus infection (SEVI)). Antibody titers to HA in serum were assessed at day 18, 28, and 35 after treatment, and HA-specific IgG and IgA were determined in bronchial lavage at day 48 post treatment. Both serum antibody titers (FIGS. 12A-12C) and HA-specific antibodies in bronchial lavage (FIGS. 12D and 12E) show a trend of enhancement in the presence of peptides 1A or 2A, consistent with a peptide-dependent increase in antigen delivery.

DETAILED DESCRIPTION

Figures 2A, 2B:
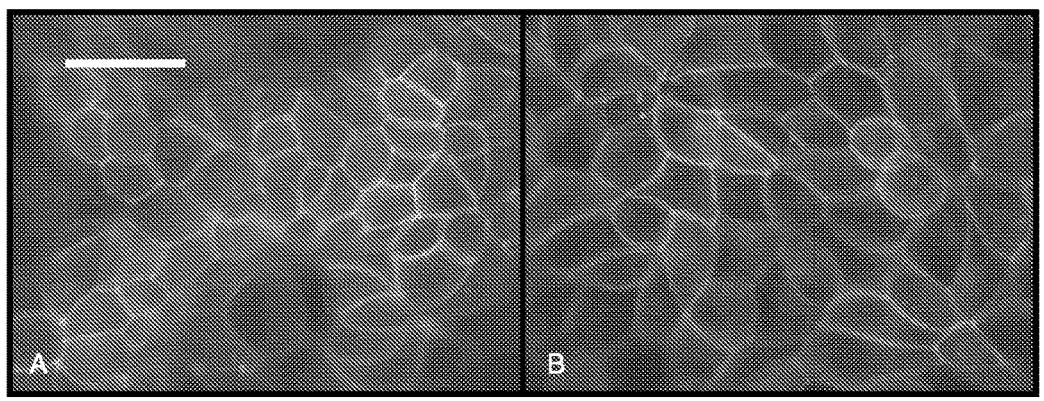
FIGS. 2A-2B show immunofluorescence microscopy images of TJ proteins in 16HBE cells. Untreated 16HBE cells were stained for: Claudin 1 (Cldn1, green) and zona occludens-1 (ZO-1, red) (FIG. 2A), as well as Claudin 4 (Cldn4, green) and occludin (Ocln, red) (FIG. 2B). The following antibodies (Invitrogen) were used: rabbit anti-Claudin1, #18-7362; mouse anti-Claudin4, #32-9400; rabbit anti-Ocln, #71-1500; mouse anti-ZO-1, #33-9100; mouse anti-Ocln, #33-1500; anti-rabbit Alexafluor®-488, #A21206; anti-rabbit Alexafluor®-568, #A10042; anti-mouse Alexafluor®-488, #A21202; anti-mouse Alexafluor®-568, #A10037. Scale bar=25 μm.

Aspects illustrated herein relate to agents that alter tight junction ("TJ") barrier function in epithelial cells, particularly in those epithelial cells expressing claudin-1 ("Cldn1"), as well as compositions and products including such agents, and uses thereof.

The term epithelia is used in its usual sense and relates to the epithelium, the outside layer of cells that covers all the free, open surfaces of the body including cutaneous (skin) and mucous membranes. The term transepithelial refers to entry of a substance such as a drug, vaccine, or active agent through the epithelium, including direct topical application and application using a support material such as a patch.

Peptides and compositions described herein are also useful in altering the permeability of blood vessels and blood brain barrier.

Accordingly, according to aspects illustrated herein, there is provided an agent that transiently disrupts claudin-1 within TJs. The agent includes a peptide having at least 40% polar, uncharged amino acid residues and a self-assembled β-sheet secondary structure.

In one embodiment, the peptide has low solubility in aqueous media in the absence of surfactant. In another embodiment, the peptide is insoluble in aqueous media in the absence of surfactant.

The peptide according to aspects illustrated herein may associate with or bind to native claudin-1 within the TJ.

In one embodiment, the peptide according to aspects illustrated herein has an amino acid sequence that is not naturally-occurring in claudin-1.

For instance, the peptide according to aspects illustrated herein may be a scrambled form of a claudin-1 amino acid sequence, where the claudin-1 amino acid sequence includes at least 6 amino acid residues of an extracellular loop region of claudin-1.

As used herein, a "scrambled" form of a peptide refers to a peptide having the same or substantially the same (i.e., one or two substitutions depending on the peptide length) amino acid content as the source or reference peptide (e.g., naturally-occurring claudin-1 fragment), but a different primary sequence of amino acid residues.

In one embodiment, the claudin-1 amino acid sequence that the scrambled peptide is derived from is a mammalian claudin-1 protein. In one embodiment, the claudin-1 amino acid sequence that the scrambled peptide is derived from is a human claudin-1 protein. The claudin-1 amino acid sequence may include one or more cysteine to serine substitutions.

In one embodiment, the scrambled peptide has the same hydrophobicity and/or pI as the peptide from which it is derived.

In one embodiment, the scrambled peptide includes the amino acid sequence of SILTGVSTLDQSLKQLSNFSQAVSTQSSR (SEQ ID NO:6), ISGVQCCQTKQSS (SEQ ID NO:10), RRGVCSSSQGRR (SEQ ID NO:11), ISMSQQVSQSGVSDKFST (SEQ ID NO:16), SIMSGKQSSVQSQVT (SEQ ID NO:17), VSMSSTSQ (SEQ ID NO:18), VSSSSQ (SEQ ID NO:19), or SILTGVST (SEQ ID NO:20).

In one embodiment, the agent according to the aspects illustrated herein includes a plurality of peptides and the plurality of the peptides forms one or more fibrils. In one embodiment, one or more of the peptides undergo spontaneous self-assembly into structured supramolecular assemblies. In another embodiment, one or more of the peptides undergo co-assembly into structured amyloid fibrils.

The amino acid sequence of the peptide according to aspects illustrated herein may include at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, or at least 90% polar uncharged amino acid residues.

In one embodiment, the amino acid sequence of the peptide according to the aspects illustrated herein includes at least one hydrophobic amino acid residue. In one embodiment, the peptide includes at least two hydrophobic amino acid residues. In one embodiment, the peptide includes at least 25% or at least 30% hydrophobic amino acid residue content. In one embodiment, the peptide includes at least 31% hydrophobic amino acid residue content.

The amino acid sequence of the peptide according to aspects illustrated herein may include an amino acid sequence of at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 amino acid residues. In one embodiment, the peptide includes an amino acid sequence of 6 to 30 amino acid residues. In one embodiment, the peptide includes an amino acid sequence of 6 to 29 amino acid residues. In one embodiment, the peptide includes an amino acid sequence of less than 53 amino acid residues.

In one embodiment, the peptide is not a polypeptide sequence of a naturally-occurring claudin 1 protein. In one embodiment, the peptide is not a polypeptide sequence of an extracellular loop domain (e.g., the second extra cellular loop domain) of a naturally-occurring claudin 1 protein. In one embodiment, the peptide is not a polypeptide sequence of a naturally-occurring claudin 1 protein, or an extracellular loop domain thereof, that includes one or more cysteine to serine substitutions.

In one embodiment, the peptide does not consist of the amino acid sequence of SSVSQSTGQIQSKVFDSLLNLNSTLQATR (SEQ ID NO:1), SCVSQSTGQIQCKVFDSLLNLNSTLQAT (SEQ ID NO:2), SSVSQSTGQIQSKVFDSLLNLSSTLQAT (SEQ ID NO:3), or SCVSQSTGQ[I/V]QCKVFDSLLNLSSTLQAT (SEQ ID NO:4).

In one embodiment, the peptide does not include the amino acid sequence of SSVSQSTGQIQSKVFDSLLNLNSTLQATR (SEQ ID NO:1), SCVSQSTGQIQCKVFDSLLNLNSTLQAT (SEQ ID NO:2), SSVSQSTGQIQSKVFDSLLNLSSTLQAT (SEQ ID NO:3), or SCVSQSTGQ[I/V]QCKVFDSLLNLSSTLQAT (SEQ ID NO:4).

The peptide according to aspects illustrated herein may include the amino acid sequence of SSVSQSTGQIQSKVFDSLLNLSSTLQATR (SEQ ID NO: 5), SILTGVSTLDQSLKQLSNFSQAVSTQSSR (SEQ ID NO:6), GGMSCVSQSTGQIQCKV (SEQ ID NO:7), SCVSQSTGQIQCKV (SEQ ID NO:8), RRGSCVSQSGRR (SEQ ID NO: 9), ISGVQCCQTKQSS (SEQ ID NO: 10), RRGVCSSSQGRR (SEQ ID NO:11), LWMSSVSQSTGQIQSKVFDS (SEQ ID NO:12), MSSVSQSTGQIQSKVFDS (SEQ ID NO:13), MSSVSQSTGQIQSKV (SEQ ID NO:14), MSSVSQST (SEQ ID NO:15), ISMSQQVSQSGVSDKFST (SEQ ID NO:16), SIMSGKQSSVQSQVT (SEQ ID NO:17), VSMSSTSQ (SEQ ID NO:18), VSSSSQ (SEQ ID NO:19), SILTGVST (SEQ ID NO:20), SSVSQSTG (SEQ ID NO:21), GQIQSKVG (SEQ ID NO:22), LNLSSTLQG (SEQ ID NO:23), NSVVQSTG (SEQ ID NO:24), GQMQSKVG (SEQ ID NO:25), or SCVSQSTGQIQCKVFDSLLNLSSTLQATR (SEQ ID NO:26). The peptide according to aspects illustrated herein may include GGGMSCVSQSTGQIQCK (SEQ ID NO:28); GGSCVSQS (SEQ ID NO:29); RRGSCVSQSTGQIQCKGRR (SEQ ID NO:30), or RRGISGVQCCQTKQSSGRR) (SEQ ID NO:31).

In one embodiment, the peptide according to aspects illustrated herein includes an additional Methionine amino acid residue at the N-terminal position. In one embodiment, the peptide includes a modified version of SEQ ID NO: 26 and includes the amino acid sequence of MSCVSQSTGQIQCKVFDSLLNLSSTLQATR (SEQ ID NO:27). This same modification can be made to any one of SEQ ID NOs: 1-31. Other modifications at the N- and/or C-terminal ends of the peptide are contemplated, including, e.g., palmitoyl-, Nyl-, Npg-, or combinations thereof. Although exemplary modifications are described, other modifications are contemplated.

Aspects illustrated herein also include peptides described herein that are in isolated form. In one embodiment, the isolated peptide includes the amino acid sequence of SSVSQSTGQIQSKVFDSLLNLSSTLQATR (SEQ ID NO:

5), SILTGVSTLDQSLKQLSNFSQAVSTQSSR (SEQ ID NO:6), GGMSCVSQSTGQIQCKV (SEQ ID NO:7), SCVSQSTGQIQCKV (SEQ ID NO:8), RRGSCVSQSGRR (SEQ ID NO: 9), ISGVQCCQTKQSS (SEQ ID NO: 10), RRGVCSSSQGRR (SEQ ID NO:11), LWMSSVSQSTGQ-IQSKVFDS (SEQ ID NO:12), MSSVSQSTGQIQSKVFDS (SEQ ID NO:13), MSSVSQSTGQIQSKV (SEQ ID NO:14), MSSVSQST (SEQ ID NO:15), ISMSQQVSQS-GVSDKFST (SEQ ID NO:16), SIMSGKQSSVQSQVT (SEQ ID NO:17), VSMSSTSQ (SEQ ID NO:18), VSSSSQ (SEQ ID NO:19), SILTGVST (SEQ ID NO:20), SSVSQSTG (SEQ ID NO:21), GQIQSKVG (SEQ ID NO:22), LNLSSTLQG (SEQ ID NO:23), NSVVQSTG (SEQ ID NO:24), GQMQSKVG (SEQ ID NO:25), or SCVSQSTGQIQCKVFDSLLNLSSTLQATR (SEQ ID NO:26). In one embodiment, the isolated peptide includes the amino acid sequence of GGGMSCVSQSTGQIQCK (SEQ ID NO:28); GGSCVSQS (SEQ ID NO:29); RRG-SCVSQSTGQIQCKGRR (SEQ ID NO:30), or RRGIS-GVQCCQTKQSSGRR) (SEQ ID NO:31).

The peptides described herein (including isolated peptides) can also be presented in the form of a fusion peptide that includes, in addition, a second amino acid sequence coupled to the inventive peptides via peptide bond. The second amino acid sequence can be a purification tag, such as poly-histidine ($His_6$-), a glutathione-S-transferase (GST-), or maltose-binding protein (MBP-), which assists in the purification but can later be removed, i.e., cleaved from the peptide following recovery. Protease-specific cleavage sites (i.e., in a cleavable linker sequence) can be introduced between the purification tag and the desired peptide. The desired peptide product can be purified further to remove the cleaved purification tags.

According to one approach, the peptides described herein can be synthesized by standard peptide synthesis operations. These include both FMOC (9-fluorenylmethyloxy-carbonyl) and tBoc (tert-butyloxy-carbonyl) synthesis protocols that can be carried out on automated solid phase peptide synthesis instruments including, without limitation, the Applied Biosystems 431 A, 433 A synthesizers and Peptide Technologies Symphony or large scale Sonata or CEM Liberty automated solid phase peptide synthesizers. The use of alternative peptide synthesis instruments is also contemplated. Peptides prepared using solid phase synthesis are recovered in a substantially pure form.

The peptides described herein may be also prepared by using recombinant expression systems followed by separation and purification of the recombinantly prepared peptides. Generally, this involves inserting an encoding nucleic acid molecule into an expression system to which the molecule is heterologous (i.e., not normally present). One or more desired nucleic acid molecules encoding a peptide described herein may be inserted into the vector. The heterologous nucleic acid molecule is inserted into the expression system or vector in proper sense (5'-3') orientation and correct reading frame relative to the promoter and any other 5' and 3' regulatory molecules.

Nucleic acid molecules encoding the peptides described herein can be prepared via solid-phase synthesis using, e.g., the phosphoramidite method and phosphoramidite building blocks derived from protected 2'-deoxynucleosides. To obtain the desired oligonucleotide, the building blocks are sequentially coupled to the growing oligonucleotide chain in the order required by the sequence of the product. Upon the completion of the chain assembly, the product is released from the solid phase to solution, deprotected, collected, and typically purified using HPLC. The limits of solid phase synthesis are suitable for preparing oligonucleotides up to about 200 nt in length, which encodes peptides on the order of about 65 amino acids or less. The ends of the synthetized oligonucleotide can be designed to include specific restriction enzyme cleavage site to facilitate ligation of the synthesized oligonucleotide into an expression vector.

For longer peptides, oligonucleotides can be prepared via solid phase synthesis and then the synthetic oligonucleotide sequences ligated together using various techniques. Recombinant techniques for the fabrication of whole synthetic genes are reviewed, for example, in Hughes et al., "Chapter Twelve—Gene Synthesis: Methods and Applications," *Methods in Enzymology* 498:277-309 (2011), which is hereby incorporated by reference in its entirety.

Once a suitable expression vector is selected, the desired nucleic acid sequences are cloned into the vector using standard cloning procedures in the art, as described by Sambrook et al., Molecular Cloning: A Laboratory Manual, Cold Springs Laboratory, Cold Springs Harbor, N.Y. (1989), or U.S. Pat. No. 4,237,224 to Cohen and Boyer, which are hereby incorporated by reference in their entirety. The vector is then introduced to a suitable host.

A variety of host-vector systems may be utilized to recombinantly express the peptides described herein. Primarily, the vector system must be compatible with the host used. Host-vector systems include, without limitation, the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used to carry out this and other aspects described herein.

When it is desirable to achieve heterologous expression of a peptide according aspects illustrated herein, then DNA molecules encoding these products can be delivered into the cell. Basically, this includes providing a nucleic acid molecule encoding the desired product, and then introducing the nucleic acid molecule into the cell under conditions effective to express the desired product in the cell. Preferably, this is achieved by inserting the nucleic acid molecule into an expression vector before it is introduced into the cell.

Purified peptides may be obtained by several methods. The peptide is may be produced in purified form (preferably at least about 80% or 85% pure, or at least about 90% or 95% pure) by conventional techniques. Depending on whether the recombinant host cell is made to secrete the peptide into growth medium (see U.S. Pat. No. 6,596,509 to Bauer et al., which is hereby incorporated by reference in its entirety), the peptide can be isolated and purified by centrifugation (to separate cellular components from supernatant containing the secreted peptide) followed by sequential ammonium sulfate precipitation of the supernatant. The fraction containing the peptide is subjected to gel filtration in an appropriately sized dextran or polyacrylamide column to separate the peptides from other proteins. If necessary, the peptide fraction may be further purified by HPLC.

Alternatively, if the peptide of interest of interest is not secreted, it can be isolated from the recombinant cells using standard isolation and purification schemes. This includes disrupting the cells (e.g., by sonication, freezing, French press, etc.) and then recovering the peptide from the cellular debris. Purification can be achieved using the centrifugation, precipitation, and purification procedures described above. The use of purification tags, described above, can simplify this process. Once the peptides described herein are recovered, they can be used to prepare a composition as described herein.

Regardless of the embodiment, agents according to aspects described herein can be administered via pharmaceutical composition or formulation. Accordingly, another aspect illustrated herein includes pharmaceutical compositions or formulations including one or more peptides or peptide agents according to aspects illustrated herein, a pharmaceutically acceptable carrier, and optionally an active agent.

Peptides or peptide agents described herein may be present in an amount suitable to disrupt TJ function in epithelial cells. For instance, the peptide agent may be present in an amount by weight of about 0.000001 to about 25%, about 0.000001 to about 20%, about 0.000001 to about 15%, about 0.000001 to about 10%, about 0.000001 to about 5%, about 0.000001 to about 4%, about 0.000001 to about 3%, about 0.000001 to about 2%, about 0.000001 to about 1%, about 0.00001 to about 25%, about 0.00001 to about 20%, about 0.00001 to about 15%, about 0.00001 to about 10%, about 0.00001 to about 5%, about 0.00001 to about 4%, about 0.00001 to about 3%, about 0.00001 to about 2%, about 0.00001 to about 1%, about 0.0001 to about 25%, about 0.0001 to about 20%, about 0.0001 to about 15%, about 0.0001 to about 10%, about 0.0001 to about 5%, about 0.0001 to about 4%, about 0.0001 to about 3%, about 0.0001 to about 2%, about 0.0001 to about 1%, about 0.001 to about 25%, about 0.001 to about 20%, about 0.001 to about 15%, about 0.001 to about 10%, about 0.001 to about 5%, about 0.001 to about 4%, about 0.001 to about 3%, about 0.001 to about 2%, about 0.001 to about 1%, about 0.01 to about 25%, about 0.01 to about 20%, about 0.01 to about 15%, about 0.01 to about 10%, about 0.01 to about 5%, about 0.01 to about 4%, about 0.01 to about 3%, about 0.01 to about 2%, about 0.01 to about 1%, about 0.1 to about 25%, about 0.1 to about 20%, about 0.1 to about 15%, about 0.1 to about 10%, about 0.1 to about 5%, about 0.1 to about 4%, about 0.1 to about 3%, about 0.1 to about 2%, or about 0.1 to about 1%. The peptide agent may be present at a concentration of less than about 500 μM, less than about 400 μM, less than about 300 μM, less than about 200 μM, less than about 100 μM, less than about 50 μM, less than about 40 μM, less than about 30 μM, less than about 20 μM, less than about 15 μM, less than about 10 μM, less than about 9 μM, less than about 8 μM, less than about 7 μM, less than about 6 μM, less than about 5 μM, less than about 4 μM, less than about 3 μM, less than about 2 μM, less than about 1 μM, less than about 0.9 μM, less than about 0.8 μM, less than about 0.7 μM, less than about 0.6 μM, less than about 0.5 μM, less than about 0.4 μM, less than about 0.3 μM, less than about 0.2 μM, less than about 0.1 μM, less than about 0.09 μM, less than about 0.08 μM, less than about 0.07 μM, less than about 0.06 μM, less than about 0.05 μM, less than about 0.04 μM, less than about 0.03 μM, less than about 0.02 μM, or less than about 0.01 μM.

As used herein, the term "active agent" means an agent that is intended to have an effect on an individual. Active agents include, without limitation, therapeutic agents that are intended for use in the diagnosis, cure, treatment, or prevention of disease. The term "drug" and "therapeutic agent" are used interchangeably and are intended to have their broadest interpretation as any therapeutically active substance which is delivered to a living organism to produce a desired, usually beneficial, effect. In general, this includes therapeutic agents in all of the major therapeutic areas including, but not limited to, antiinfectives, antibiotics, antiviral agents, analgesics, fentanyl, sufentanil, buprenorphine, analgesic combinations, anesthetics, anorexics, antiarthritics, antiasthmatic agents, terbutaline, anticonvulsants, antidepressants, antidiabetic agents, antidiarrheals, antihistamines, antiinflammatory agents, antimigraine preparations, antimotion sickness, scopolamine, ondansetron, antinauseants, antineoplastics, antiparkinsonism drugs, cardiostimulants, dobutamine, antipruritics, antipsychotics, antipyretics, antispasmodics, gastrointestinal and urinary, anticholinergics, sympathomimetics, xanthine derivatives, cardiovascular preparations, calcium channel blockers, nifedipine, beta-blockers, beta-agonists, salbutamol, ritodrine, antiarrythmics, antihypertensives, atenolol, ACE inhibitors, diuretics, vasodilators, coronary, peripheral and cerebral, central nervous system stimulants, cough and cold preparations, decongestants, diagnostics, hormones, parathyroid hormone, growth hormone, insulin, hypnotics, immunosuppressives, muscle relaxants, parasympatholytics, parasympathomimetics, anti-oxidants, nicotine, prostaglandins, psychostimulants, sedatives, tranquilizers, skin acting antioxidants, caretenoids, ascorbic acid (vitamin C), vitamin E, anti wrinkling agents, retinoids, retinol (vitamin A alcohol), alpha-hydroxic acids, beta-hydroxy acid, salicylic acid, combination-hydroxy acids and poly-hydroxy acids, and hydrolyzed and soluble collagen, hyaluronic acid, anticellulite agents, aminophyllines, skin bleaching agents, retinoic acid, hydroquinone, peroxides, botanical preparations or extracts, and combinations thereof. Additional therapeutic agents include one or more antigenic agents that are present in a vaccine composition. Antigenic agents may include proteins or polypeptides, nucleic acids, lipids, carbohydrates, lipopolysaccharides, etc., which are intended to induce an immune response against a pathogen, infected cell, or cell characterized by a disease state (e.g., cancerous cell).

The term "pharmaceutically acceptable carrier" refers to any suitable adjuvants, carriers, excipients, or stabilizers, and can be in solid or liquid form such as tablets, capsules, powders, solutions, suspensions, or emulsions. In certain embodiments according to aspects illustrated herein, the carrier may be in the form of a lotion, cream, gel, emulsion, ointment, solution, suspension, foam, or paste.

In one embodiment, the carrier includes an oil-in water emulsion. In one embodiment, the carrier includes tromethane ethanol, polyethylene glycol, glycerin, propylene glycol, acrylates, Carbopol, purified water, benzyl alcohol, cetyl alcohol, citric acid, monoglycerides, diglycerides, triglycerides, oleyl alcohol, sodium cetostearylsulphate, sodium hydroxide, stearyl alcohol, white petrolatum, mineral oil, propylene carbonate, white wax, paraffin, or any combination thereof.

Compositions and/or carriers according to aspects illustrated herein may also be in the form of aqueous solutions that include a surfactant, particularly when the agents that alter TJ barrier function are insoluble or only partially soluble in the aqueous carriers. Suitable surfactants according to aspects illustrated herein include, for example, nonionic surfactant polyols. In one embodiment, the surfactant is Pluronic® F-127. Other known surfactant or solubilizer additives may be used. Examples include, but are not limited to, solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic® F-127, Pluronic® F-68 (polyoxyethylene polyoxypropylene block copolymers), PEG (polyethylene glycol), non-ionic surfactants such as polysorbate 20 or 80 or poloxamer 184 or 188, Pluronic® polyls, other block co-polymers, and chelators such as EDTA and EGTA.

Compositions according to aspects illustrated herein may also include lung surfactant formulations tailored for delivery to the lung epithelium. For instance, suitable formulations that may be modified for use in accordance with aspects illustrated herein include those described in WO 2013/120058 and WO 2008/011559, which are hereby incorporated by reference in their entirety. Such compositions may readily form liposomal vesicles that can be used to deliver all classes of agents described herein to a patient. The administration of such compositions can be any suitable approach for delivery of the therapeutic agent to a target tissue, including aspiration, airway instillation, aerosolization, nebulization, intranasal instillation, oral or nasogastric instillation, intraperitoneal injection, or intravascular injection. The target tissue can be lung tissue or a systemic tissue. The agent or agents to be delivered can be any pharmaceutical or therapeutic agent including those described herein.

Surfactants and/or additives described herein may be used alone or in combination in amounts by weight of, for example, about 0.001 to about 5.0%, about 0.001 to about 4.0%, about 0.001 to about 3.0%, about 0.001 to about 2.0%, about 0.001 to about 1.0%, about 0.005 to about 5.0%, about 0.005 to about 4.0%, about 0.005 to about 3.0%, about 0.005 to about 2.0%, about 0.005 to about 1.0%, about 0.01 to about 5.0%, about 0.01 to about 4.0%, about 0.01 to about 3.0%, about 0.01 to about 2.0%, about 0.01 to about 1.0%, about 0.025 to about 5.0%, about 0.025 to about 4.0%, about 0.025 to about 3.0%, about 0.025 to about 2.0%, about 0.025 to about 1.0%, about 0.05 to about 5.0%, about 0.05 to about 4.0%, about 0.05 to about 3.0%, about 0.05 to about 2.0%, or about 0.05 to about 1.0%. In one embodiment, the composition comprises about 0.12% surfactant (e.g., Pluronic® F-127). In one embodiment, the composition comprises about 0.006% surfactant (e.g., Pluronic® F-127).

Compositions according to aspects illustrated herein may include a suitable carrier, as described above. The pharmaceutical compositions may be formulated for administrating topically (as described above with respect to transepithelial, transdermal or transmucosal formulations) or by any other means suitable. For example, the compositions may be formulated for administration orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes. The formulations may conveniently be presented in unit dosage form and may be prepared by any of the methods well known in the art of pharmacy. Carrier(s) may be present in an amount by weight of, for example, about 10 to about 99%, about 20 to about 99%, about 30 to about 99%, about 40 to about 99%, about 50 to about 99%, about 60 to about 99%, about 70 to about 99%, about 80 to about 99%, about 90 to about 99%.

Compositions described herein include a peptide as described herein along with one or more of a pharmaceutically acceptable carrier, surfactant, and optionally one or more therapeutic agents, as described above. For example, the carrier may be present in the amount of 40-99% by weight, the surfactant may be present in an amount of up to 5% by weight of the composition, and the peptide may be present in an amount of about 0.000001 to about 25% by weight of the composition.

Typically, a composition will contain from about 0.01 to about 90 percent (e.g., up to about 1, 5, 10, 20, 30, 40, 50, 60, 70, 80, or 90 percent) by weight of active agent(s)), together with the adjuvants, carriers, and/or excipients. For instance, the therapeutic agent may present in an amount by weight of about 0.01 to about 90%, about 0.01 to about 80%, about 0.01 to about 70%, about 0.01 to about 60%, about 0.01 to about 50%, about 0.01 to about 40%, about 0.01 to about 30%, about 0.01 to about 20%, about 0.01 to about 10%, or about 0.01 to about 5%, 0.1 to about 90%, about 0.1 to about 80%, about 0.1 to about 70%, about 0.1 to about 60%, about 0.1 to about 50%, about 0.1 to about 40%, about 0.1 to about 30%, about 0.1 to about 20%, about 0.1 to about 10%, or about 0.1 to about 5%.

While individual needs may vary, determination of optimal ranges of effective amounts of each component is within the skill of the art. Typical dosages of the therapeutic agent comprise about 0.01 to about 100 mg/kg·body wt. Other dosages may comprise about 0.1 to about 100 mg/kg·body wt. or about 1 to about 100 mg/kg·body wt. Treatment regimen for the administration of the agents can also be determined readily by those with ordinary skill in art. That is, the frequency of administration and size of the dose can be established by routine optimization, preferably while minimizing any side effects.

Compositions and/or carriers according to aspects illustrated herein may include an artificial vesicle. The artificial vesicle may be any suitable artificial vesicle known to those of skill in the art. In certain embodiments according to aspects illustrated herein, the artificial vesicle may be a microparticle, nanoparticle, or the like. Such will be known to those of skill in the art and may include any suitable materials (e.g., BSA, polymer microgels silica). In one embodiment, the artificial vesicle is a liposome or a micelle.

Liposomes are vesicles comprised of one or more concentrically ordered lipid bilayers which encapsulate an aqueous phase. They are normally not leaky, but can become leaky if a hole or pore occurs in the membrane, if the membrane is dissolved or degrades, or if the membrane temperature is increased to the phase transition temperature. Current methods of drug delivery via liposomes require that the liposome carrier ultimately become permeable and release the encapsulated drug at the target site. This can be accomplished, for example, in a passive manner wherein the liposome bilayer degrades over time through the action of various agents in the body. Every liposome composition will have a characteristic half-life in the circulation or at other sites in the body and, thus, by controlling the half-life of the liposome composition, the rate at which the bilayer degrades can be somewhat regulated.

In contrast to passive drug release, active drug release involves using an agent to induce a permeability change in the liposome vesicle. Liposome membranes can be constructed so that they become destabilized when the environment becomes acidic near the liposome membrane (see, e.g., Proc. Natl. Acad. Sci. USA 84:7851 (1987); Biochemistry 28:908 (1989), each of which is hereby incorporated by reference in its entirety). When liposomes are endocytosed by a target cell, for example, they can be routed to acidic endosomes which will destabilize the liposome and result in drug release.

Alternatively, the liposome membrane can be chemically modified such that an enzyme is placed as a coating on the membrane, which enzyme slowly destabilizes the liposome. Since control of drug release depends on the concentration of enzyme initially placed in the membrane, there is no real effective way to modulate or alter drug release to achieve "on demand" drug delivery. The same problem exists for pH-sensitive liposomes in that as soon as the liposome vesicle comes into contact with a target cell, it will be engulfed and a drop in pH will lead to drug release.

Different types of liposomes can be prepared according to Bangham et al., *J. Mol. Biol.* 13:238-252 (1965); U.S. Pat. No. 5,653,996 to Hsu et al.; U.S. Pat. No. 5,643,599 to Lee et al.; U.S. Pat. No. 5,885,613 to Holland et al.; U.S. Pat. No. 5,631,237 to Dzau et al.; and U.S. Pat. No. 5,059,421 to Loughrey et al., each of which is hereby incorporated by reference in its entirety.

Like liposomes, micelles have also been used in the art for drug delivery. A number of different micelle formulations have been described in the literature for use in delivery proteins or polypeptides, and others have been described which are suitable for delivery of nucleic acids. Any suitable micelle formulations can be adapted for delivery of the therapeutic protein or polypeptide or nucleic acids aspects illustrated herein. Exemplary micelles include without limitation those described, e.g., in U.S. Pat. No. 6,210,717 to Choi et al.; and U.S. Pat. No. 6,835,718 to Kosak, each of which is hereby incorporated by reference in its entirety.

Another aspect illustrated herein is a transepithelial (e.g., transdermal or transmucosal) drug formulation. The drug formulation includes a pharmaceutically acceptable carrier, an effective amount of a therapeutic agent, and an agent that transiently disrupts claudin-1 within tight junctions according to aspects illustrated herein.

Aspects illustrated herein are also useful in the controlled delivery of polypeptide and protein drugs and other macromolecular drugs. These macromolecular substances typically have a molecular weight of at least about 300 daltons, and more typically a molecular weight in the range of about 300 to 40,000 daltons. In one embodiment, the therapeutic is at least 300 daltons in size. In another embodiment, the therapeutic is at least 500 daltons in size. In yet a further embodiment, the therapeutic is not less than 300 daltons in size.

Specific examples of peptides, proteins, and macromolecules in this size range include, without limitation, LHRH, LHRH analogs such as buserelin, gonadorelin, napharelin and leuprolide, GHRH, GHRF, insulin, insulotropin, heparin, calcitonin, octreotide, endorphin, TRH, NT-36 (chemical name: N=[[(s)-4-oxo-2-azetidinyl]carbonyl]-L-histidyl-L-prolinamide), liprecin, pituitary hormones (e.g., HGH, HMG, HCG, desmopressin acetate, etc.), follicle luteoids, αANF, growth factors such as growth factor releasing factor (GFRF), βMSH, somatostatin, atrial natriuretic peptide, bradykinin, somatotropin, platelet-derived growth factor, asparaginase, bleomycin sulfate, chymopapain, cholecystokinin, chorionic gonadotropin, corticotropin (ACTH), epidermal growth factor, erythropoietin, epoprostenol (platelet aggregation inhibitor), follicle stimulating hormone, glucagon, hirulog, and other analogs of hirudin, hyaluronidase, interferon, insulin-like growth factors, interleukin-1, interleukin-2, menotropins (urofollitropin (FSH) and LH), oxytocin, streptokinase, tissue plasminogen activator, urokinase, vasopressin, desmopressin, ACTH analogs, ANP, ANP clearance inhibitors, angiotensin II antagonists, antidiuretic hormone agonists, antidiuretic hormone antagonists, bradykinin antagonists, CD4, ceredase, CSF's, enkephalins, FAB fragments, IgE peptide suppressors, IGF-1, neuropeptide Y, neurotrophic factors, oligodeoxynucleotides and their analogues such as antisense RNA, antisense DNA and anti-gene nucleic acids, opiate peptides, colony stimulating factors, parathyroid hormone and agonists, parathyroid hormone antagonists, prostaglandin antagonists, pentigetide, protein C, protein S, ramoplanin, renin inhibitors, thymosin alpha-1, thrombolytics, TNF, vaccines, vasopressin antagonist analogs, alpha-1 anti-trypsin (recombinant), and TGF-beta.

Accordingly, another aspect illustrated herein relates to a method of administering a pharmaceutical composition as described herein. The method involves applying a pharmaceutical composition as described herein to an epithelial site on a subject. Also contemplated is a method of administering a transepithelial drug formulation to a subject. The method involves applying a transepithelial drug formulation according to aspects illustrated herein to an epithelial site on a subject.

Alternatively, the pharmaceutical composition can be a vaccine. In one embodiment, the vaccine is a transepithelial vaccine formulation that would benefit from TJ disruption at the site of vaccine delivery. The transepithelial vaccine formulation may be a formulation suitable for administration to any epithelial site, including cutaneous (e.g., transdermal formulation) and mucous membranes. In one embodiment, the transepithelial vaccine formulation is a transdermal vaccine formulation. The transdermal vaccine is often presented in the form of a patch worn by the user, whereby moisture from the vaccine recipient's body allows for delivery of the active agents across the skin (i.e., at the site of application).

The transepithelial vaccine formulations of aspects illustrated herein may include a pharmaceutically suitable carrier, an effective amount of an antigen or antigen-encoding nucleic acid molecule present in the carrier, optionally one or more adjuvants, and an agent that transiently disrupts claudin-1 function within tight junctions according to aspects illustrated herein. The formulation is presented in the transepithelial delivery vehicle, as is known in the art.

Vaccination at, for example, the epidermal surface may be accomplished by targeting Langerhan cells in the epidermis with agents according to aspects illustrated herein. Similar strategies have been used to target M cells in mucosal surfaces with claudin-4 specific peptides (Lo et al., "M Cell Targeting by a Claudin 4 Targeting Peptide Can Enhance Mucosal IgA Responses," *BMC Biotech.* 12:7 (2012), which is hereby incorporated by reference in its entirety).

Any suitable antigen or antigen-encoding nucleic acid molecule, or a combination thereof, can be used in the vaccine formulations of aspects illustrated herein. Exemplary classes of vaccine antigen include, without limitation, an allergen, an immunogenic subunit derived from a pathogen, a virus-like particle, an attenuated virus particle, or glycoprotein or glycolipid conjugated to an immunogenic polypeptide. Antigen-encoding nucleic acid molecules can be in the form of naked DNA or expression vectors, as well as infective transformation vectors.

In certain embodiments, the antigen (e.g., allergen) is coupled to the adjuvant.

A number of known transepithelial vaccine formulations can be modified to include an agent that alters TJ barrier function in epithelial cells.

One exemplary transdermal vaccine formulation that can be modified is described in U.S. Pat. No. 6,420,176 to Lisziewicz et al., which is hereby incorporated by reference in its entirety. For example, the carrier may comprise one or more of sugar, polylysine, polyethylenimine, polyethylenimine derivatives, and liposomes, together with their derivatives. One preferred carrier of this type is a mannosylated polyethylenimine. The DermaVir transdermal delivery system is believed to employ these types of carriers.

Another exemplary transdermal vaccine formulation that can be modified is described in U.S. Pat. No. 6,869,607 to Buschle et al., which is hereby incorporated by reference in its entirety. For example, the carrier may comprise a solution or emulsion that is substantially free of inorganic salt ions and includes one or more water soluble or water-emulsifiable substances capable of making the vaccine isotonic or hypotonic (e.g., maltose, fructose, galactose, saccharose, sugar alcohol, lipid; or combinations thereof), and an adjuvant that is a polycation (e.g., polylysine or polyarginine) optionally modified with a sugar group. The adjuvant, according to one embodiment, can be a combination of a polycation and an immunostimulatory CpG or non-CpG oligodeoxynucleotide. One form of this adjuvant is the Intercell adjuvant IC31.

Yet another exemplary vaccine formulation that can be modified is described in U.S. Pat. No. 7,247,433 to Rose, which is hereby incorporated by reference in its entirety. For example, HPV virus-like particles could be administered with a pharmaceutically acceptable carrier and with or without *E. coli* LT R192G as the adjuvant.

As noted above, formulations (including vaccine formulations) according to aspects illustrated herein may be delivered via aspiration, airway instillation, aerosolization, nebulization, intranasal instillation, oral or nasogastric instillation, intraperitoneal injection, or intravascular injection. Pulmonary delivery of vaccine formulations according to aspects illustrated herein may be carried out according to techniques known to those of skill in the art (see, e.g., Lu et al., "Pulmonary Vaccine Delivery," *Expert Rev. Vaccines* 6(2): 213-226 (2007), which is hereby incorporated by reference in its entirety). An exemplary vaccine formulation that can be modified is described in U.S. Patent Application Publication No. 2013/0183336, which is hereby incorporated by reference in its entirety. Suitable devices for delivering vaccine formulations according to aspects illustrated herein include, for example, nebulizers (see, e.g., U.S. Patent Application Publication No. 2013/0032140, which is hereby incorporated by reference in its entirely).

As noted above, such vaccine formulations according to aspects illustrated herein may include surfactants. In addition to those noted above, suitable surfactants for use in accordance with aspects illustrated herein include those that are suitable for use in vaccine formulations suitable for pulmonary delivery (see, e.g., Lu et al., "Pulmonary Vaccine Delivery," *Expert Rev. Vaccines* 6(2): 213-226 (2007), WO 2013/120058, and WO 2008/011559, which are hereby incorporated by reference in their entirety).

Accordingly, a further aspect of aspects illustrated herein relates to a method of administering a transepithelial vaccine formulation to a subject. The method involves applying the transepithelial vaccine formulation of aspects illustrated herein to an epithelial site on the subject.

The region of epithelia (e.g., skin) to be treated in accordance with aspects illustrated herein is dependent on the intended purpose for delivery. For instance, for transdermal drug or vaccine delivery, the drug or vaccine may be administered to a region of the skin such as the upper arm, back, or the like. The drug or vaccine may also be administered via other routes as described herein.

Yet another aspect of aspects illustrated herein relates to a transdermal delivery device or patch. The transdermal drug delivery device includes an agent or a transdermal vaccine or drug formulation according to aspects illustrated herein. In one embodiment, the transdermal patch includes a backing material, an adhesive material in contact with a first portion of the backing material; and a drug storage material comprising the agent or transdermal vaccine or drug formulation, where the drug storage material is in contact with a second portion of the backing material. In one embodiment the patch also includes a releasable liner material to be removed upon application to the skin.

Any suitable backing material known in the art of transdermal patches (such as a breathable material) may be used in accordance with aspects illustrated herein. The backing is flexible such that the device conforms to the skin. Exemplary backing materials include conventional flexible backing materials used for pressure sensitive tapes, such as polyethylene, particularly low density polyethylene, linear low density polyethylene, high density polyethylene, polyester, polyethylene terephthalate, randomly oriented nylon fibers, polypropylene, ethylene-vinyl acetate copolymer, polyurethane, rayon and the like. Backings that are layered, such as polyethylene-aluminum-polyethylene composites, are also suitable. The backing should be substantially inert to the ingredients of the drug storage material.

Adhesives suitable for use with aspects illustrated herein with any dermatologically acceptable adhesive. Examples of dermatologically acceptable adhesives include, but are not limited to acrylics, natural and synthetic rubbers, ethylene vinyl acetate, poly(alpha-olefins), vinyl ethers, silicones, copolymers thereof and mixtures thereof. In an embodiment, the first adhesive layer includes a silicone adhesive (e.g., BIO-PSA 7-4302 Silicone Adhesive available commercially from Dow Corning®).

The transdermal patch may optionally include one or more release liners for storage or handling purposes. Many suitable release liners are known within the art. The release liner can be made of a polymeric material that may be optionally metallized. Examples of suitable polymeric materials include, but are not limited to, polyurethane, polyvinyl acetate, polyvinylidene chloride, polypropylene, polycarbonate, polystyrene, polyethylene, polyethylene terephthalate (PET), polybutylene terephthalate, paper, and combinations thereof. In certain embodiments, the release liner is siliconized. In other embodiments, the release liner is coated with fluoropolymer, such as PET coated with fluoropolymer (e.g., SCOTCHPAK™ 9744 from 3M™).

The drug storage material may be any dermatologically acceptable material suitable for use as a drug storage material or reservoir in a transdermal patch. For instance, the drug storage material may be a polymer. Examples of polymers include microporous polyolefin film (e.g., SOLUPOR® from SOLUTECH™), acrylonitrile films, polyethylnapthalene, polyethylene terephthalate (PET), polyimide, polyurethane, polyethylene, polypropylene, ethylene-vinyl acetate (EVA), copolymers thereof and mixtures thereof. In one embodiment, the polymer is EVA. In another embodiment, the polymer is EVA having a vinyl acetate content by weight in the range of about 4% to about 19%. In a preferred embodiment, the polymer is EVA having vinyl acetate content by weight of about 9%. The drug storage material may also include a heat-sealable material for attaching to other components. As an example, the heat-sealable permeable layer may be an EVA membrane, such as COTRAN™ 9702, available commercially from 3M™.

Figure 13A:
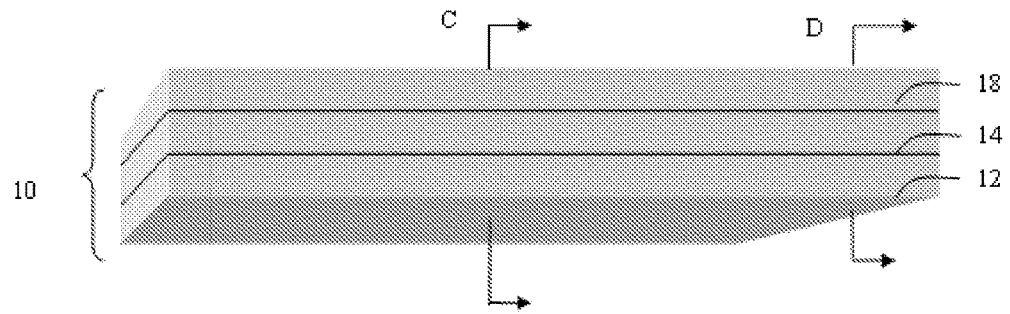
FIGS. 13A-13D show bottom perspective (FIG. 13A) and cross sectional (FIGS. 13B, 13C, and 13D) views of one embodiment of a transdermal patch according to aspects illustrated herein.
Figure 13B:
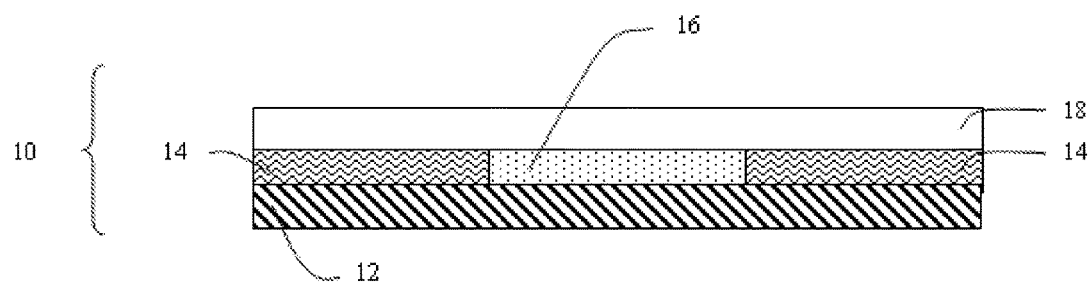
Figure 13C:
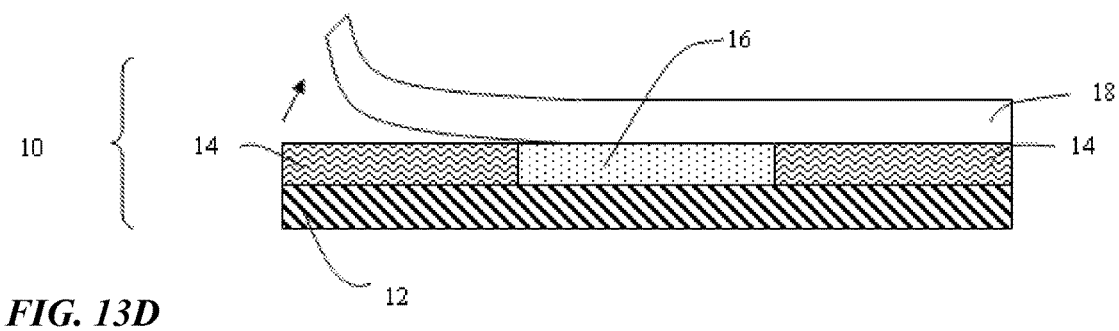
Figure 13D:
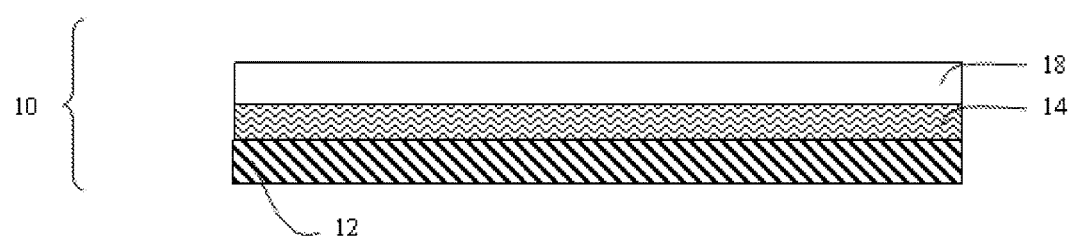

Referring now to FIGS. 13A to 13D, FIG. 13A is a perspective view of one embodiment of a transdermal patch according to aspects illustrated herein. FIG. 13B is a cross-section of transdermal patch 10 along axis C of FIG. 13A. In one embodiment, transdermal patch 10 includes backing 12, adhesive material 14, and drug storage material 16. In addition, transdermal patch 10 may optionally include releasable liner 18, which is removed upon application to skin, as shown in FIG. 13C. FIG. 13D is a cross-sectional view of transdermal patch 10 along axis D of FIG. 13A.

Other delivery devices including compositions according to aspects illustrated herein are also contemplated. Such devices include those suitable for delivery of compositions according to aspects illustrated herein via aspiration, airway instillation, aerosolization, nebulization, intranasal instillation, oral or nasogastic instillation, intraperitoneal injection, or intravascular injection. Exemplary devices include inhalers or nebulizers (see, e.g., U.S. Patent Application Publication No. 2013/0032140, which is hereby incorporated by reference in its entirely).

Another aspect illustrated herein relates to a method of disrupting an epithelial barrier. The method involves applying to an epithelial site an amount of an agent according to aspects illustrated herein that is effective to disrupt claudin-1 in keratinocytes present at the site, thereby disrupting barrier formation at the epithelial site. Also contemplated are methods of disrupting an epithelial barrier by applying to an epithelial site a pharmaceutical composition described herein, thereby disrupting barrier formation at the epithelial site.

EXAMPLES

The following examples are provided to illustrate embodiments of subject matter claimed herein, but are by no means intended to limit its scope.

Materials and Methods for Examples

Materials

Tentagel Rink Amide resin, Rapp Polymere; Fmoc amino acids and activators, P3 Biosystems or Advanced Chemtech; dry DMF and piperidine, AlfaAesar; DIPEA, TCI America; cell culture media, EdU kit, and fluorescence labeling reagents were from Life Technologies (Gibco, Invitrogen); antibodies, Invitrogen; WST1, Clon Clontech; Transwells, Corning; Biotin, propargyl amine, KBr, Pluronic F-127® and all other reagents were from Sigma.

Peptide Synthesis:

Standard solid phase Fmoc peptide synthesis methods were used. Peptide 1 (R-SSVSQSTGQIQSKVFDSLLN-LSSTLQATR-NH$_2$) (SEQ ID NO:5) and a corresponding scrambled sequence, peptide 2 (R-SILTGVSTLDQSLKQL-SNFSQAVSTQSSR-NH$_2$) (SEQ ID NO: 6) were synthesized with either a free N-terminus (a) or biotin-N-propargyl glycine tag (b) for subsequent labeling. Tentagel Rink Amide resin (0.25 mmol/g, 90 μm mesh size, Rapp Polymere) was loaded by hand at room temperature (5 eq. Fmoc-R, 4.9 eq. HBTU, 10 eq. DIPEA, double coupling). Aβ$_{40}$ was synthesized on Tentagel Wang (0.3 mmol/g, 90 μm mesh size, Rapp Polymere) and FKFE$_2$ (FKFEFKFE-NH$_2$) on polystyrene MBHA Rink amide resin (0.2 mmol/g, 90 μm mesh size, Adv. Chemtech). Fmoc solid phase peptide synthesis was performed on a Liberty CEM microwave synthesizer using double or triple couplings after β-branched residues and either HBTU (for Peptide 2) or HATU (for Peptide 1) as an activator. For unlabeled peptides, the terminal Fmoc was removed and the N-terminus was left unprotected. For labeled peptides, Nyl was added by submonomer peptoid synthesis: resin for labeled peptides was washed with amine-free DMF, bromoacetylated with 20 eq. bromoacetic acid and 24 eq. diisopropylcarbodiimide for 20 minutes, washed with amine-free DMF and DCM, and bromine displaced with propargyl amine (20 eq.). Biotin was double coupled using 2.5 eq. biotin, 2.45 eq. HATU, 5 eq. DIPEA in 5:4:1 NMP/DMF/DMSO.

Peptides were cleaved with 70% trifluoroacetic acid/28% DCM/1% triisopropylsilane/1% H$_2$O for one hour, the resin washed with neat TFA and pooled with cleavage cocktail. TFA was removed by rotary evaporation and peptide collected by ether precipitation. Peptides were stored at −80° C. until purification. Peptide pellets were dissolved in minimal DMSO and then denatured in 7.2 M guanidine HCl (≥25% DMSO) with sonication at 55° C. for 20 minutes. Denatured crude was incubated at 55° C. until high pressure liquid chromatography ("HPLC") purification (Waters semi-preparative C18 column at 55° C. on a Shimadzu LD-6A HPLC) using an H$_2$O/acetonitrile gradient containing 0.1% TFA. Analytical HPLC (C18 column at 55° C. using a Shimadzu LC-2010A HPLC) to assess purity could only be obtained immediately following purification. Peptides were ≥90% pure. Analytical HPLC of 1a and 1b, as well as 2a and 2b was performed. While both peptides run as single peaks by analytical HPLC immediately after purification, neither 1a nor 2a was detectable by analytical HPLC after preparation in Pluronic F-127®. This behavior is typical of self-assembling peptides, which spontaneously form structure too large to enter the analytical C18 column. Reliable disaggregation of the self-assembled material was not achievable by the standard methods used for other amyloids, such as TFA/HFIP or NaOH (LeVine "Alzheimer's β-Peptide Oligomer Formation at Physiologic Concentrations," *Anal. Biochem.* 335:81-90 (2004); Teplow, "Preparation of Amyloid β-Protein for Structural and Functional Studies," In *Methods in Enzymology Amyloid, Prions, and Other Protein Aggregates, Part C.* Elsevier Academic Press, Boston, pp 20-33, (2006); Zhao et al., "Amyloid-β Peptide Is a Substrate of the Human 20S Proteasome," *ACS Chem. Neurosci.* 1:655-660 (2010); Cao et al., "Ester to Amide Switch Peptides Provide a Simple Method for Preparing Monomeric Islet Amyloid Polypeptide under Physiologically Relevant Conditions and Facilitate Investigations of Amyloid Formation," *J. Am. Chem. Soc.* 132:4052-4053 (2010), which are hereby incorporated by reference in their entirety). Peptides 1a and 2a contain only a single phenylalanine ($\epsilon_{257.5}$=195 cm$^{-1}$/M), and the use of Pluronic F-127® precludes analysis at 214 nm by UV spectrophotometry. Therefore, peptide concentrations were determined after solubilization by BCA assay.

Mass was determined by matrix assisted laser desorption/ ionization-time of flight ("MALDI-TOF") mass spectrometry (using α-cyano-4-hydroxycinnamin acid matrix and linear, positive mode on a Bruker Autoflex III). Purified peptides were lyophilized for storage. MALDI-MS of Peptide 1a measured a monoisotopic mass of 3080.59 and an observed mass ((m+1)/z) of 3085.42. MALDI-MS of Peptide 2a measured a monoisotopic mass of 3080.59 and an observed mass ((m+1)/z) of 3084.80. MALDI-MS of labeled Peptide 1b measured a monoisotopic mass of 3401.71 and an observed mass ((m+1)/z) of 3405.10. MALDI-MS of labeled Peptide 2b measured a monoisotopic mass of 3401.71 and an observed mass ((m+1)/z) of 3407.22.

Before use, peptide fibrils were prepared in sterile, filtered phosphate buffered saline containing 0.12% Pluronic F-127® by sonication at 55° C. for 20 minutes. Peptide concentrations were determined by BCA assay (Pierce). 20× peptide stocks were prepared in 0.12% pluronic F-127/PBS, then diluted 20× into phosphate buffer, PBS or DMEM containing 1% heat-inactivated fetal bovine serum and incubated at 37° C. for 18-24 hours before cell exposure or biophysical analysis, maintaining a constant surfactant concentration (0.006% Pluronic® F127) for vehicle and peptide samples.

Circular Dichroism (CD)

2 mM peptide stocks were prepared in 10 mM phosphate buffer, pH 7.4, containing 0.12% Pluronic® F-127. These stocks were diluted with 1 mM phosphate buffer, pH 7.4 to 100 μM and 1 μM and incubated for 3 days at 25° C. Spectra were obtained at 25° C. in quartz cuvettes on an Aviv CD spectrophotometer, scanning for 4 s per 2.0 nm step using a 2.0 nm bandwidth. Data were not smoothed.

Fourier Transform Infrared Spectroscopy (FTIR) and X-ray Diffraction (XRD)

Peptide fibrils (100 μM) were incubated for one week at 37° C. in PBS, harvested by centrifugation, washed with 2 mM HCl and duplicate samples lyophilized. For FTIR, KBr pellets were prepared and 512 scans were taken on a Shimadzu FTIR spectrometer using 2 cm$^{-1}$ resolution. Background was subtracted and spectra were normalized; no smoothing was applied. Powder diffraction studies were performed on a Bruker X8 APEX II X-ray diffractometer at the Cornell Center for Materials Research.

Transmission Electron Microscopy (TEM) and Peptide Crystals

10 μL of 120 μM mature fibrils in PBS were applied to 200-mesh carbon coated copper grids for 5 minutes. Grids were washed with distilled water three times to remove excess salts and stained with 10 μL filtered 5% uranyl acetate for 5 minutes. Excess solution was removed by capillary action after each step and grids were dried before use. Fibrils were imaged using a Hitachi 7650 transmission electron microscope in high-contrast mode using an accelerating voltage of 80 kV. Peptide crystals were grown at 4° C. in inverted drops containing PBS with 25% glycerol and 0.02-0.04% Pluronic F-127®.

Thioflavin T

Peptide stocks were prepared in 0.12% Pluronic F-127®/PBS and equilibrated at room temperature for 48 hours. These stocks were diluted 20-fold into 10 μM Thioflavin T in PBS or DMEM containing 1% serum and stored at 4° C. for 24 hours. Fluorescence was measured in Greiner μ-clear bottom 384-well plates on a Tecan M1000 fluorescence plate reader ($\lambda_{ex}$=450 nm and $\lambda_{em}$=482 nm, with a 10 nm slit width).

Cell Culture

Human bronchial epithelial cells (16HBE) were grown on collagen-coated polystyrene in DMEM containing 10% heat inactivated fetal bovine serum, 10 mM HEPES, penicillin, streptomycin, and amphotericin with fresh media every 2-3 days. Cells were plated at the indicated density and grown for the indicated period. Peptides were diluted 20× into DMEM (Gibco #31053 containing 2 mM L-glutamine but lacking phenol red) containing 1% heat-inactivated fetal bovine serum and incubated at 37° C. for 18 hours before exposure. Pluronic F-127 concentrations (0.006% in cell culture media) were consistent between vehicle controls and peptide-containing samples. Cells were acclimated to the same media for 18 hours before peptide exposure.

Figure 3A:
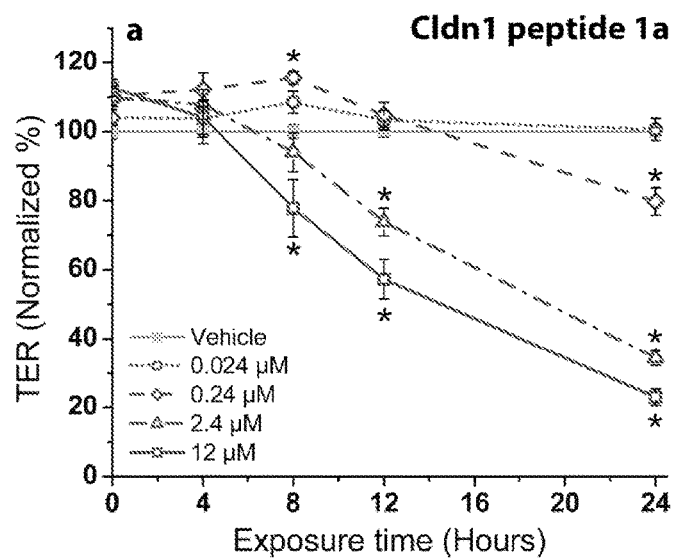
FIGS. 3A-3E are graphs depicting experimental results of transepithelial electrical resistance ("TER") and permeability assays for peptide 1a (Cldn1 peptide) and 2a (Scrambled peptide), which show a dose dependent reduction in barrier function. TER (FIGS. 3A and 3B) was measured during peptide exposure. Data were normalized to the vehicle control (n=8).
Figure 3B:
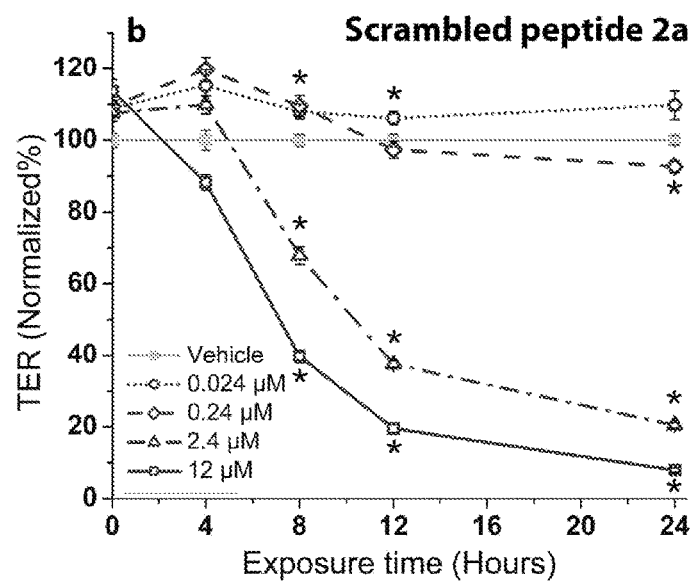
Figure 3C:
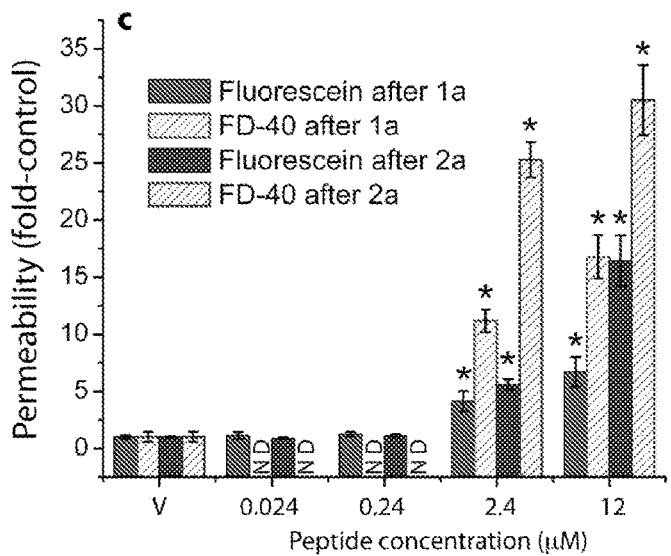
Figure 3E:
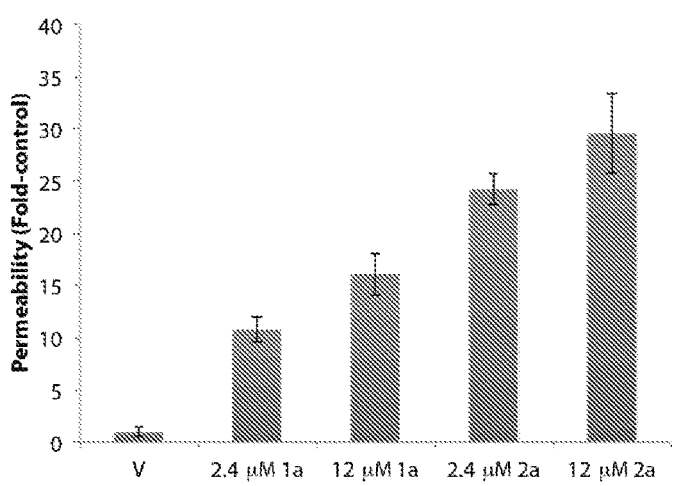
Figure 4A:
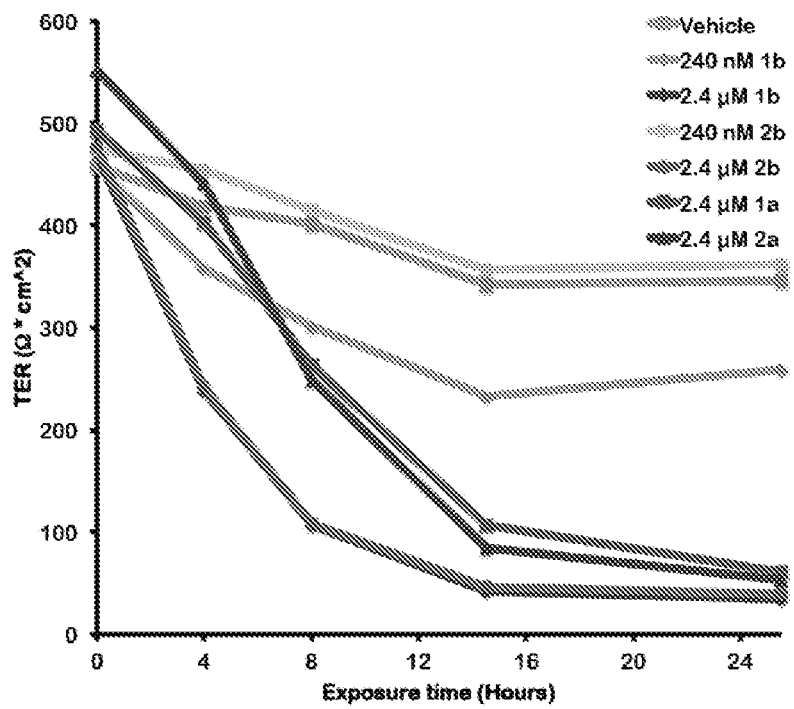
FIGS. 4A-4B are graphs depicting experimental results of TER and permeability assays for labeled peptides 1b and 2b. The results in FIG. 4A indicate that labeled peptides cause disruption of barrier, as measured by decreased TER. A representative experiment (n=2) is shown.
Figure 4B:
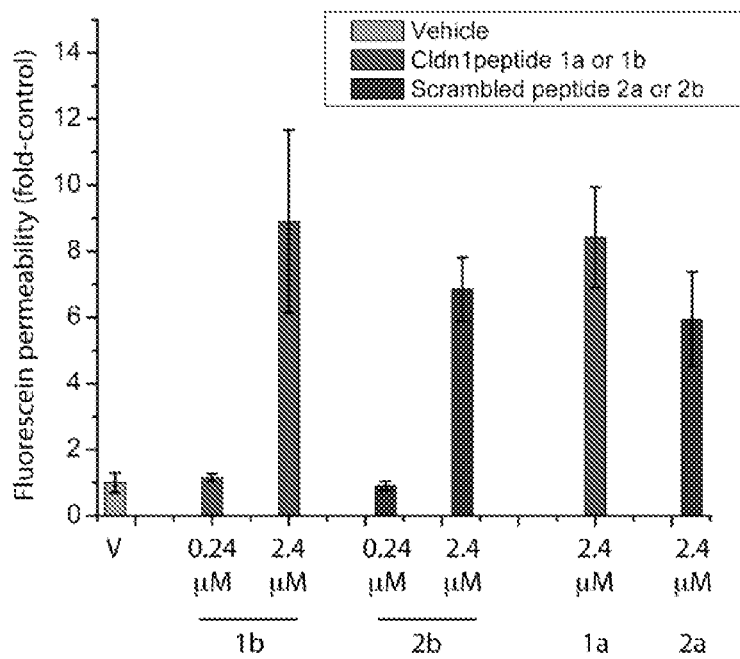

Functional Assays:

For transepithelial electrical resistance (TER) and permeability experiments, the results of which are shown in FIGS. 4A-4B, respectively, cells were plated at a density of 75,000 per 0.33 cm$^2$ transwell (Corning TW, 0.4 μM pore, polyester) and grown for 5-6 days before acclimation/peptide exposure. TER measurements were taken with chopstick electrodes using a World Precision Instruments voltohmeter, and are expressed as the measured (cellular resistance—resistance of a TW insert with no cells)/surface area of the TW insert. TER was measured before peptide exposure (time=0) and at the indicated time points thereafter. After the 24 hour measurement, a control TW was lysed with 1% Triton X-100. For permeability flux assay, 1/10 volume of 0.2% sodium fluorescein or a mixture of 40 kD FITC-dextran (600 μg/mL final apical concentration) and Alexafluor®-568 labeled Synagis monoclonal antibody was added to the apical chamber and cells were incubated at 37° C. for 30 minutes or 18 hours. Synagis monoclonal antibody was labeled with Alexafluor®-568-succinimidyl ester according to the manufacturer's instructions, unreacted fluorophor removed using centrifugal filtration, and labeled antibody resuspended in PBS containing FITC-labeled 40 kD dextran. Fluorescence in the basolateral media was read in a Tecan M1000 fluorescence plate reader using Greiner μ-clear bottom 384-well plates ($\lambda_{ex}$=494 nm and $\lambda_{em}$=512 nm for fluorescein and FITC-dextran and $\lambda_{ex}$=578 nm and $\lambda_{em}$=605 nm for Alexafluor®-568 using a 10 nm slit width). Results are shown in FIG. 3E. Error is presented as the standard error of the mean, and significance relative to the vehicle control indicated where P<0.05 using a two-tailed t-test. For TER and fluorescein permeability experiments, n=8. For barrier recovery after peptide washout and FD-40 and Alexafluor®-labeled monoclonal antibody ("AF-mAb") permeability, n=4.

Cytotoxicity:

For cytotoxicity measurements, cells were plated with a density of 7,500 per well in a 96-well plate and grown for one day before acclimation in DMEM containing 1% heat-inactivated fetal bovine serum. Cells were exposed to vehicle or peptide for 4, 12 or 24 hours. Control cells were lysed with 1% Triton X-100 for 15 minutes as a negative control. 10× WST1 stock (Clontech) was added to each well, and cells incubated for 12 minutes at 37° C. Media was removed and WST1 absorbance immediately read on a Perkin Elmer UV/Vis plate reader (WST1 $A_{450}$–background $A_{620}$). Error is presented as the standard error of the mean, and significance relative to the untreated control indicated (P<0.05). For cytotoxicity experiments, n=4. Representative data is presented.

Immunofluorescence:

For immunohistochemical labeling, cells were plated at a density of 1.2×10$^5$ cells per 1.2 cm$^2$ coverslip in a 12-well plate and cultured in DMEM containing 10% heat-inactivated fetal bovine serum for 4-5 days. One day before peptide exposure, media was changed to DMEM/1% serum. Cells were exposed to peptide for 4 or 12 hours at 37° C. Cover slips were washed three times with PBS containing calcium (Gibco), fixed in cold methanol and blocked with 1% bovine serum albumin before staining Fluorophor was conjugated to propargyl-glycine labeled peptides using a ClickIt EdU kit according to the manufacturer's instructions (omitting cell exposure to EdU). For immunofluorescent staining, cells were incubated for one hour with primary antibodies (1:500 polyclonal anti-claudin 1 antibody and 1:400 monoclonal anti-occludin), washed with PBS and stained with Alexafluor®-488 anti-rabbit and Alexafluor®-568 anti-mouse secondary antibodies (1:1000). The Cldn1 antibody used recognized an epitope at the C-terminus and did not cross react with peptides. Coverslips were mounted in Vectastain containing DAPI and imaged on an Olympus BX60 fluorescence microscope. Cldn1 and Ocln images were taken using SPOT software with no further digital manipulation.

Example 1

Characterization of Structured Peptides and Disruption of Tight Junctions in Epithelial Cells To gain insight into the structure of TJ-disrupting peptides and their mechanism of action, the biological and biophysical characteristics of the homologous human peptide hCldn1 (53-81, C54,64S) (SEQ ID NO:5) (referred to herein as "1a" or Peptide "1a") was examined. It was found that, when solubilized in the presence of surfactant, 1a disrupts TJs in cultured cells at a concentration two orders of magnitude lower than previously reported for Cldn1 peptides (Mrsny et al., "A Key Claudin Extracellular Loop Domain Is Critical for Epithelial Barrier Integrity," Am. J. Path. 172:905-915 (2008); Zwanziger et al., "A Peptidomimetic Tight Junction Modulator to Improve Regional Analgesia," Mol. Pharm. 9:1785-1794 (2012), which are hereby incorporated by reference in their entirety). Biophysical characterization indicates that la can form amyloid-like fibrils rich in β-sheet secondary structure. A previously unknown scrambled peptide (referred to herein as "2a" or Peptide "2a") with identical amino acid content, hydrophobicity and pI relative to 1a, but random sequence, also adopts a β-sheet conformation, forms fibrils and disrupts TJ.

When prepared directly in buffer or cell culture media, peptide 1a (see FIGS. 1A-1B) was not well behaved. Self-supporting organogels formed in dimethyl sulfoxide. Although the scrambled peptide 2a was initially designed as a negative control, this peptide showed similar physical behavior to 1a, forming aggregates in buffer alone and also organogels in DMSO. Screening a series of surfactants to facilitate the formation of stable peptide structure to improve handling revealed that inclusion of 0.12% Pluronic® F-127 (Khattak et al., "Pluronic F127 as a Cell Encapsulation Material: Utilization of Membrane-Stabilizing Agents," Tissue Eng. 11:974-983 (2005), which is hereby incorporated by reference in its entirety) allowed for solubilization and subsequent dilution of either 1a or 2a into buffer or cell culture media without visible precipitation.

Human bronchial epithelial cells (16HBE) were used to model TJ barrier function. 16HBE cells develop a TJ barrier (transepithelial electrical resistance, TER=800-1500 $\Omega{*}cm^2$ in 10% heat-inactivated calf serum) that persists for 14 days. 16HBE cells serve as a more robust epithelial TJ barrier model than primary human keratinocytes, which achieve varying degrees of terminal differentiation (e.g. TJ barrier function) and this declines within 24 hours. In the low serum media used for peptide exposure, 16HBE cells achieved 350-500 $\Omega{*}cm^2$ TER which was stable for 3-4 days. Cell surface expression of Cldn1, Cldn4, Ocln, and ZO-1 were consistently observed by immunofluorescence staining (FIGS. 2A-2B).

Peptides were applied apically to intact TJ barriers to model topical application. Both peptides 1a and 2a showed dose dependent barrier disruption of 16HBE TJs (FIGS. 3A-3C). A statistically significant ($P<0.05$) decrease in TER was observed with 1a concentrations as low as 240 nM by 24 hours or by 8 hours with 12 µM 1a. A 65.9±6.9% drop in TER after 24 hours incubation with 2.4 µM la coincided with increases in the permeability of labeled probes of 4.1±0.9-fold (fluorescein, 0.4 kDa) and 11.2±0.9-fold (FITC-dextran, 40 kDa ("FD-40")). 12 µM 1a enhanced the permeability for fluorescein and FD-40 by 6.7±1.3-fold and 16.8±1.9-fol, respectively.

The scrambled peptide 2a, having the same size, pI, and amino acid composition, but a unique sequence, also disrupted TJ barrier in a dose dependent manner. Exposure to 2.4 µM 2a for 24 hours decreased TER by 80±2.4%, and correspondingly increased fluorescein permeability 5.6±0.4-fold and FD-40 permeability 25.3±1.6-fold. Exposure to 12 µM 2a elicited almost complete TJ disruption, with a 92±1.6% decrease in TER, a 16.4±2.2-fold increase in fluorescein permeability and a 30.5±3.0-fold increase in FD-40 permeability after 24 hours exposure. This result demonstrates that the scrambled peptide was as effective as the Cldn1-based sequence 1a for TJ disruption.

Previous reports described the application of 100-300 µM of homologous rat Cldn1 peptides bilaterally to achieve comparable TER and fluorescein permeation effects (Mrsny et al., "A Key Claudin Extracellular Loop Domain Is Critical for Epithelial Barrier Integrity," Am. J. Path. 172:905-915 (2008); Zwanziger et al., "A Peptidomimetic Tight Junction Modulator to Improve Regional Analgesia," Mol. Pharm. 9:1785-1794 (2012), which are hereby incorporated by reference in their entirety). It is possible that the increased potencies observed in these experiments are due to differences in peptide conformation that might result from peptide handling methods. The protocol described herein brings the peptide-based approach to barrier disruption into a more practical concentration range.

Figure 3D:
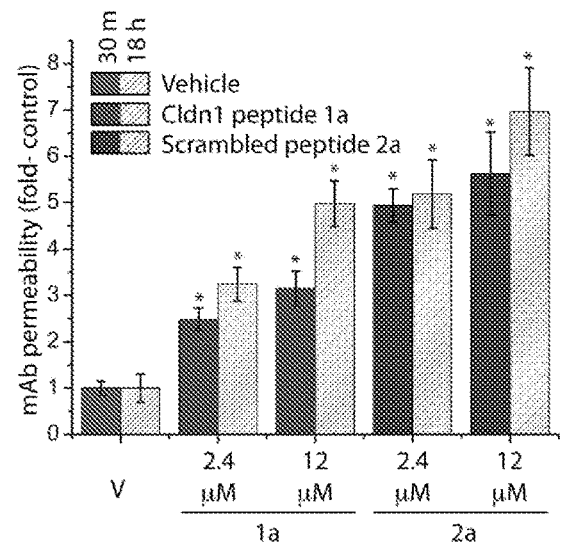

Permeation of a labeled therapeutic antibody (Synagis, 168 kD) was also enhanced by peptide-mediated TJ disruption (FIG. 3D). Antibody penetration was enhanced 2.5±0.2-fold and 3.2±0.4-fold by 2.4 and 12 µM peptide 1a, respectively. Again, slightly better permeation was observed using peptide 2a, with 4.9±0.4-fold and 5.6±0.9-fold enhancement using 2.4 and 12 µM, respectively.

Figure 5A:
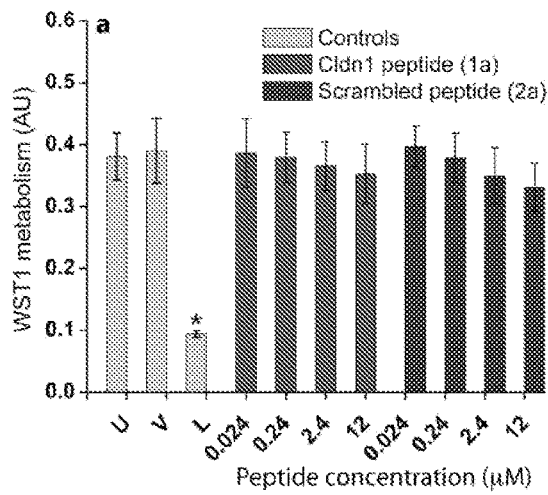
FIGS. 5A-5C are bar graphs of experimental results.
Figure 5B:
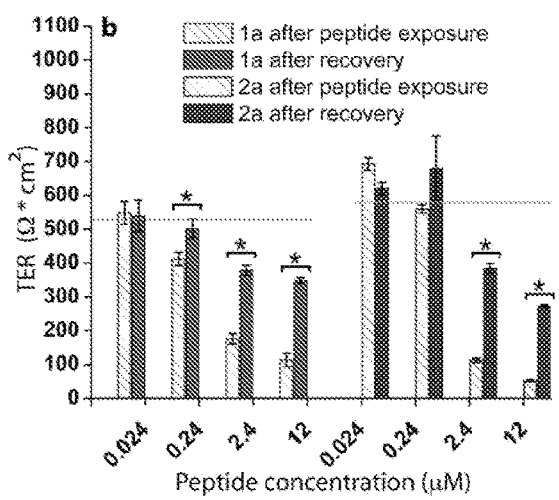

The Pluronic F-127® surfactant which was added to the vehicle to ensure the peptides went into solution did not disrupt TJs, as evidenced by in the lack of effect on TER or permeability assays ("Vehicle", FIGS. 3A-3D and 4A). Unrelated peptides tested in the same concentration range (2-12 µM monomeric $A\beta_{40}$ or $(FKFE)_2$) also did not decrease TER. To ensure that barrier disruption was not due to cytotoxic effects, sub-confluent cultures were exposed to peptides or vehicle for 1, 4, 12 (representative experiment shown in FIG. 5A) or 24 hours. No statistically significant differences in WST1 metabolism were seen at any peptide concentration or exposure time. After peptide or vehicle was washed out, TER values gradually increased, indicating that 16HBE cultures recover barrier function (FIG. 5B). Together, these results indicate that TJ disruption is peptide specific and not cytotoxic to 16HBE cultures.

Figures 6A, 6B, 6C, 6D, 6E, 6F, 6G, 6H:
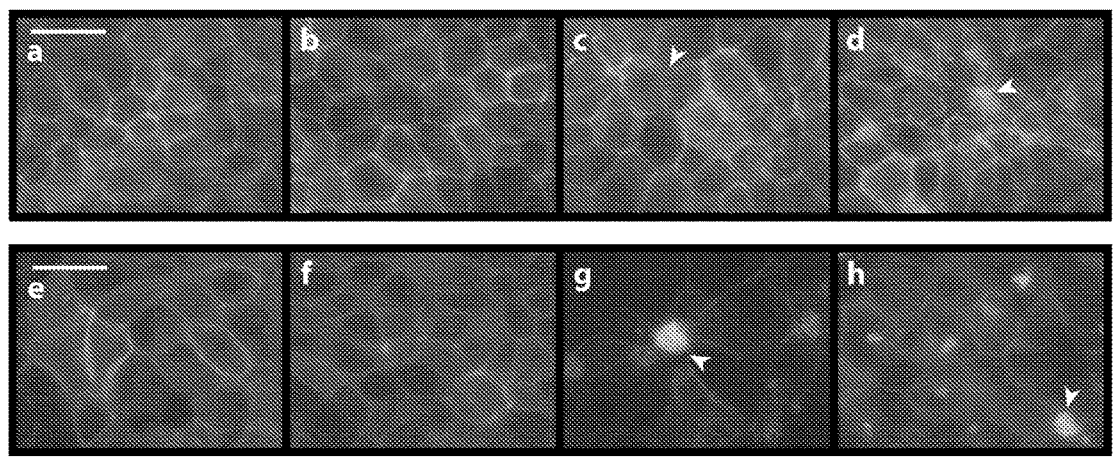
FIG. 6A-6H show immunofluorescence images demonstrating CLDN1 peptide 1a and scrambled peptide 2a disrupt TJs in 16HBE cultures. Immunofluorescence imaging of endogenous Cldn1 (green) and Ocln (red) overlay at TJs (FIGS. 6A-6D). Labeled (red) Cldn1 peptide (1b) and scrambled (2b) co-localize with endogenous Cldn1 (green) in 16HBE cultures after 4 hours exposure (FIGS. 6E-6H). The images correspond to the cultures incubated with the following.

Using immunofluorescence staining, it was noted that both peptides 1a and 2a induced similar changes in TJ protein localization (FIGS. 6A-6H). The characteristic honeycomb patterning of Cldn1 and Ocln was apparent in untreated or vehicle-treated cells. It was observed that Cldn1 and Ocln localization was disturbed 12 hours after exposure to 1a or 2a (FIGS. 6C and 6D). Disruptions to the TJ staining at the cell periphery coincide with aggregates and/or diffuse Cldn1 staining. The size and number of these regions of mislocalized Cldn1 and Ocln increased with peptide concentration. These images confirm that the TJ network is disrupted in regions with disturbed Cldn1 localization.

To gain insight into the mechanism for TJ disruption, labeled peptides 1b and 2b were synthesized. Peptides 1b and 2b were constructed with an N-terminal tag containing an N-propargyl glycine residue for bioorthogonal labeling through copper catalyzed cycloaddition subsequent to peptide exposure. It was thought that this approach would be least likely to alter the self-assembly characteristics of the peptide as opposed to the direct addition of a fluorophor.

It was expected that labeled peptides to bind to TJ structures at the cell boundaries and co-localize in the characteristic honeycomb pattern (akin to that observed by Mrsny et al. for rat Cldn1 (53-80) (Mrsny et al., "A Key Claudin Extracellular Loop Domain Is Critical for Epithelial Barrier Integrity," Am. J. Path. 172:905-915 (2008), which is hereby incorporated by reference in its entirety). Alternatively, they could co-localize with Cldn1 in a punctate staining pattern indicative of endocytosis, as observed by Zwanziger et al. (Zwanziger et al., "Claudin-Derived Peptides are Internalized Via Specific Endocytosis Pathways," *Ann. NY Acad. Sci.* 1257:29-37 (2012), which is hereby incorporated by reference in its entirety), who reported that a TAMRA-labeled rat Cldn1 (53-81, C54,64S) was endocytosed through a combination of clathrin-mediated uptake and macropinocytosis within the first hour of exposure. Instead, both 1b and 2b formed polydisperse, μm-scaled aggregates associated with cells, even at concentrations as low as 240 nM. Little to no punctate staining of co-localized peptide and cellular Cldn1 was observed at early time points. After 4 hours incubation, some cellular Cldn1 co-localized with peptide aggregates. In many cases, gaps were observed in the cellular Cldn1 honeycomb pattern at the cell periphery surrounding the labeled peptide clusters (FIGS. 6G and 6H), strongly indicative of TJ disruption. The observed peptide-dependent effects on barrier function result from changes to Cldn1 localization, rather than peptide directly intercalating into intact TJ structures, was inferred. Given these results, further characterization of the biophysical properties of 1a and 2a and their self-assembled structures was warranted. Both peptides 1a and 2a spontaneously formed fibrils in PBS (with a final Pluronic® F-127 concentration of 0.006%). Fibrils of 1a (FIGS. 7A and 7C) were uniform, 8.2±0.7 nm wide with no apparent twist, and frequently clustered into aligned bundles. Fibrils of 2a were 4.1±0.4 nm in width (FIGS. 7B and 7D), but adopted a different morphology, having slight twists and forming twisted bundles of two or more strands and web-like arrays of these twisted bundles. Fibrils as long as 1 μm were observed in both preparations by TEM.

Figures 7A, 7B, 7C, 7D, 7E, 7F:
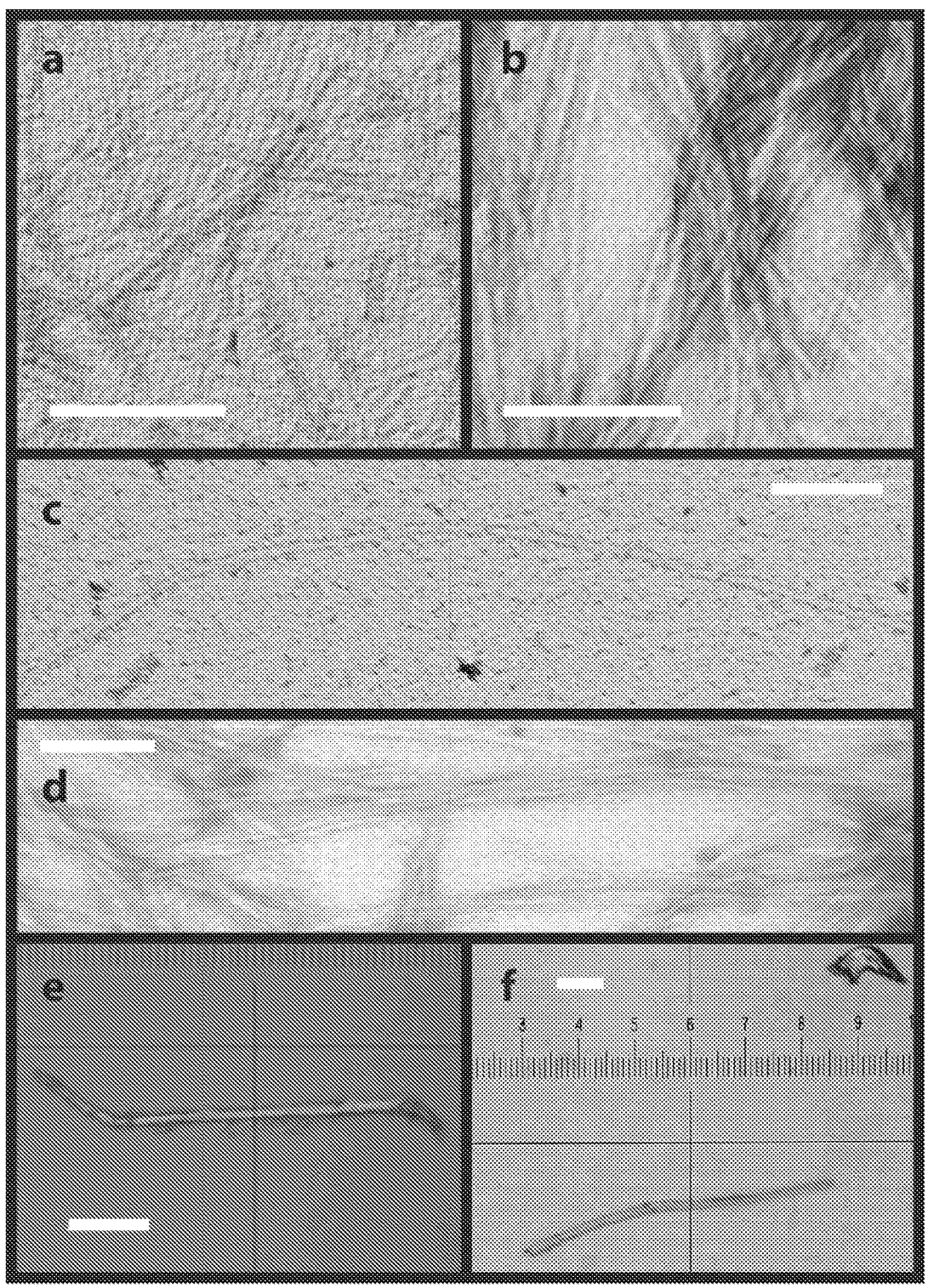
FIGS. 7A-7F are images showing peptides 1a (Cldn1) and 2a (Scrambled) form fibrils up to 1 µm in length visualized by TEM and needle-like crystals up to 680 µm in length within hours. The following are shown: 1a (FIGS. 7A, 7C, and 7E) and 2a (FIGS. 7B, 7D, and 7F): TEM (FIGS. 7A-7D), scale bar=100 nm; crystals (FIGS. 7E and 7F), scale bar=100 µm.
Figure 8A:
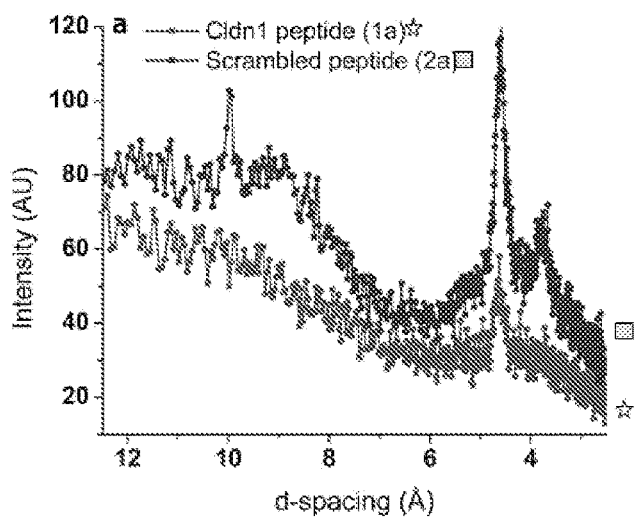
FIGS. 8A-8E are graphs of results showing fibrils of 1a (star) and 2a (square) have β-sheet structure FIG. 8A-8C, as well as graphs showing results of CD experiments (FIG. 8D) and FITR spectra of labeled peptides 1b and 2b (FIG. 8E). X-ray powder diffraction of lyophilized fibrils (FIG. 8A) indicates d-spacings of 4.6 Å, characteristic of the periodic backbone spacing in extended β-sheet structure. Significant β structure is evident by the minima at 218 nm in circular dichroism (FIG. 8B). The amide I peak at 1628 $cm^{-1}$ in the FTIR transmission spectra (FIG. 8C) is characteristic of antiparallel β-sheets.
Figure 9:
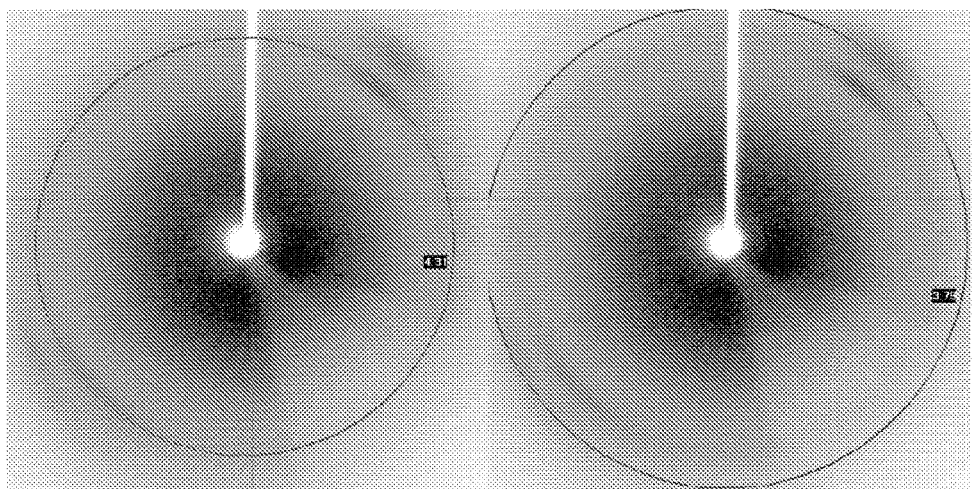
FIG. 9 shows the X-ray diffraction of peptide 1a crystals (in-house X-ray source). Crystals were grown in PBS containing 25% glycerol for 24 hours. Both planar and needle-like crystals gave similar diffraction patterns, with 4.3 (left) and 3.7 (right) Å reflections highlighted.

When diluted to 200-300 μM in PBS or PBS containing glycerol as a cryoprotectant, crystals of 1a formed within hours (FIG. 7E). Both needle and plate crystalline forms were observed. Crystals of 1a gave a fibril diffraction pattern with 4.3 Å and 3.7 Å reflections in an X-ray source (FIG. 9), but diffraction was of insufficient quality to enable high-resolution structure determination. X-ray powder diffraction (XRD, FIG. 8A) yielded similar patterns for 1a and 2a. Both showed 4.6 Å d-spacing, characteristic of extended β-sheet, while peptide 2a had the additional 9.9 Å reflection indicative of cross-β structure. Limited crystallinity of the 1a sample precluded resolution of this reflection. The additional 3.9 Å reflection in 2a indicates a periodic twist in the cross-β structure (Inouye et al., "Structure of Core Domain of Fibril-Forming PHF/Tau Fragments," *Biophys. J.* 90:1774-1789 (2006), which is hereby incorporated by reference in its entirety) consistent with the fibrils observed TEM.

Figure 8B:
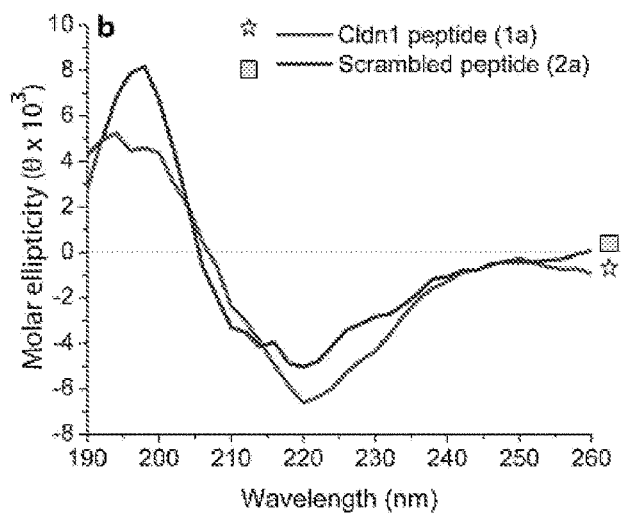
Figure 8C:
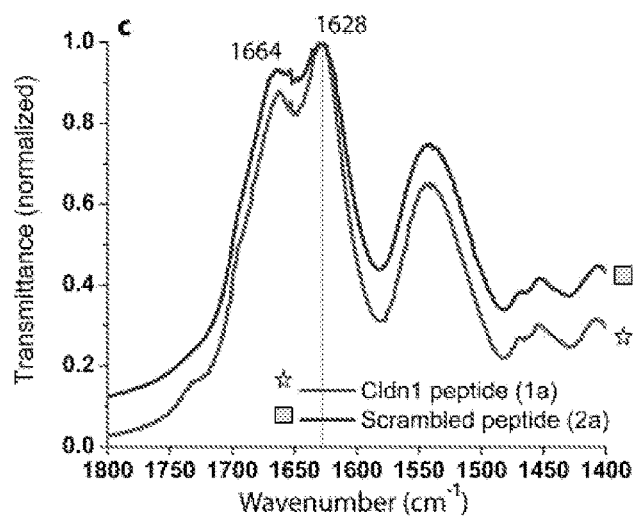
Figure 8D:
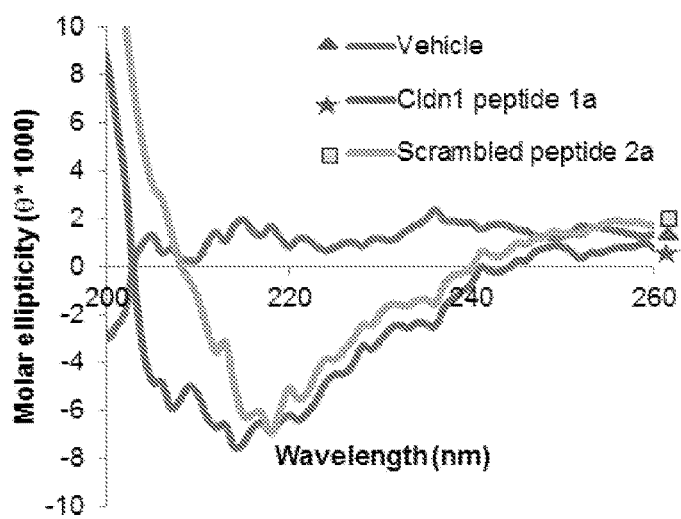

Significant secondary structure was observed by circular dichroism (CD) for both peptides 1a and 2a when they were solubilized in Pluronic® F-127 and diluted into PBS (FIG. 8B). The minima at 220 nm may indicate the presence of multiple secondary structural elements, such as α/β or β-sheet/β-turn, rather than a strictly α-helical conformation (for which minima at 210 and 222 nm are expected) or exclusively β-sheet conformation (expected minimum 215-218 nm). Similar circular dichroism spectra were observed for both 1a and 2a at concentrations as low as 1 μM (FIG. 8D), which represent the detection limit of the spectrometer used. This result implies either that these peptides are structured in their monomeric form, or that the critical concentration ($C_r$) is exceedingly low (for comparison, $C_r$ for Aβ$_{42}$ is about 1 μM (Hu et al., "Amyloid Seeds Formed by Cellular Uptake, Concentration, and Aggregation of the Amyloid-Beta Peptide," *Proc. Nat'l. Acad. Sci. U.S.A.* 106: 20324-20329 (2009), which is hereby incorporated by reference in its entirety)). It is believed that the exemplary threshold concentrations for peptides 1 and 2 are <1 μM; the functional activity of peptide 1a at 240 nM indicates that its $C_r$ could be even lower. The amphipathic environment provided by the surfactant or membranes could play a role in structure formation. Surfactant could significantly alter fibril equilibrium and ultrastructural character compared to water-soluble fibrils.

Figure 8E:
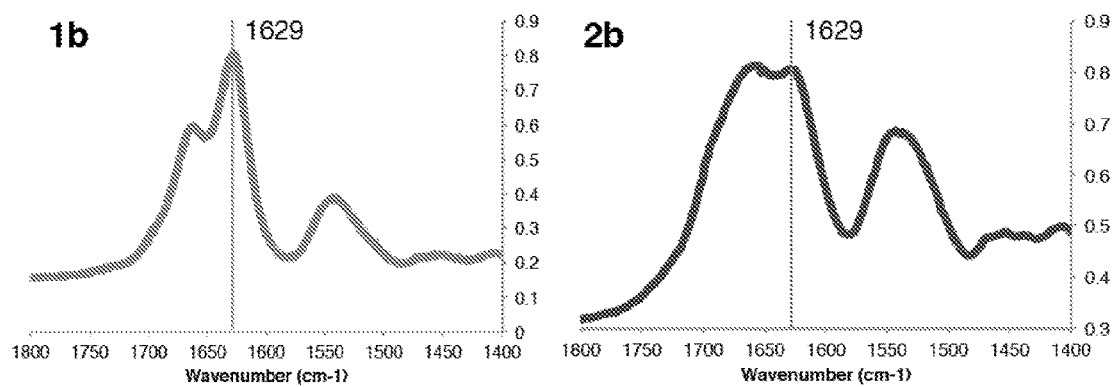

As another line of evidence to confirm β-sheet structure, FTIR spectra of lyophilized fibrils of both 1a and 2a were virtually identical (FIG. 8C), with peaks at 1664 cm$^{-1}$ and 1628 cm$^{-1}$. Uncoupled backbone carbonyl groups typically show a peak around 1650 cm$^{-1}$ in the amide I region of FTIR spectra. The shift from 1650 cm$^{-1}$ to 1628 cm$^{-1}$ indicates vibrational coupling of carbonyl oxygens through their alignment in extended β-sheets (Zandomeneghi et al., "FTIR Reveals Structural Differences Between Native β-Sheet Proteins and Amyloid Fibrils," *Prot. Sci.* 13:3314-3321 (2009); Shivu et al., "Distinct β-Sheet Structure in Protein Aggregates Determined by ATR-FTIR Spectroscopy," *Biochem.* 52 (31): 5176-5183 (2013), which are hereby incorporated by reference in their entirety). A peak around 1694 cm$^{-1}$ is sometimes observed for antiparallel β-sheets, but this peak was not obvious. The amide II peak at 1544 cm$^{-1}$ supports the presence of ordered secondary structure. FTIR spectra of labeled peptides 1b and 2b are shown in FIG. 8E.

Figure 10A:
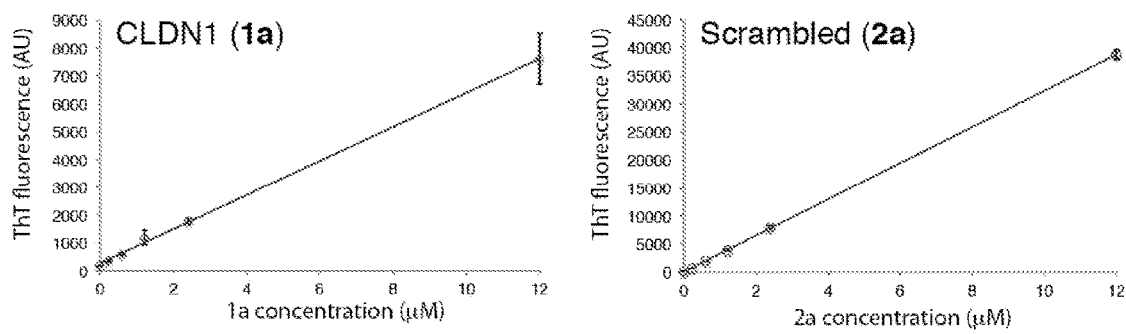
FIGS. 10A-10B are graphs showing results of Thioflavin T binding of 1 and 2. 20× peptide stocks were prepared in 0.12% pluronic® F-127 and incubated 24 hours at room temperature. Stocks were diluted in either PBS (FIG. 10A) or DMEM (FIG. 10B) media containing 1% serum containing 10 µM thioflavin T and incubated at 4° C. for 48 hours before fluorimetry. All concentrations tested showed significant statistically significant thioflavin T fluorescence compared to the vehicle control (P<0.005, n=4). Error bars represent standard deviations. Note that the Y-axes are not on the same scale.
Figure 10B:
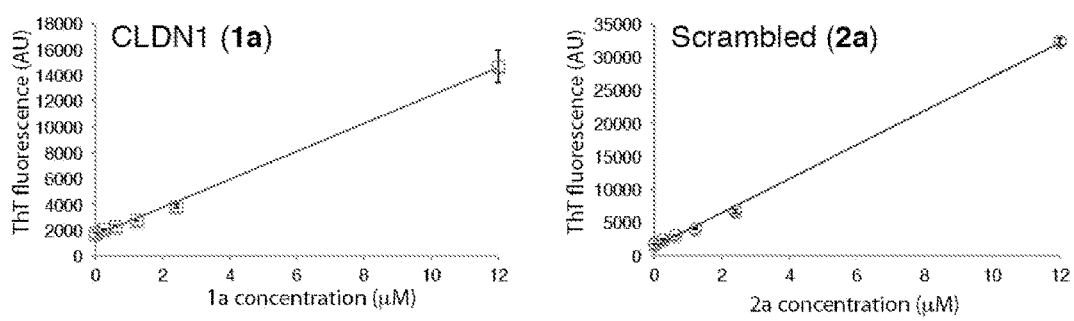
Figure 11A:
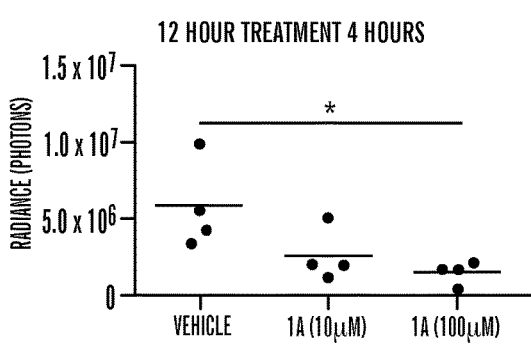
FIGS. 11A-11F are graphs illustrating experimental results of luciferase permeability experiments. Mice (4 mice per group) were treated after anesthetization in the nasal cavity with vehicle alone (0.006% Pluronic F127 in saline) or with varying concentrations of peptide. After 12 or 24 hours, a solution of 10 micrograms luciferase was applied. Mice were then imaged at various time points to determine the amount of luciferase remaining in the nasal cavity.
Figure 11B:
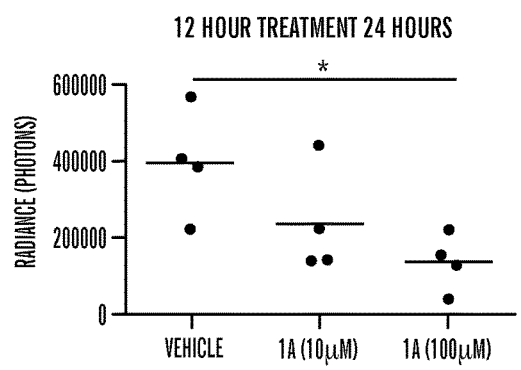
Figure 11C:
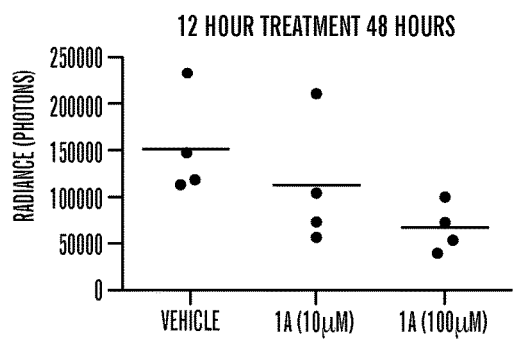
Figure 11D:
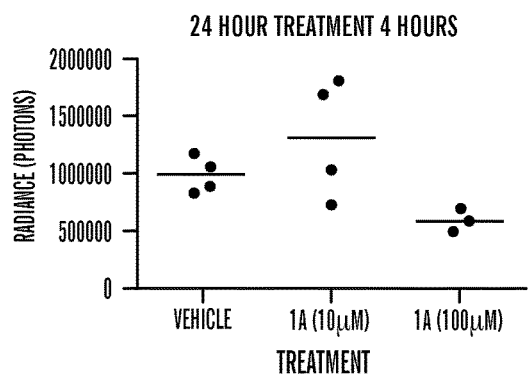
Figure 11E:
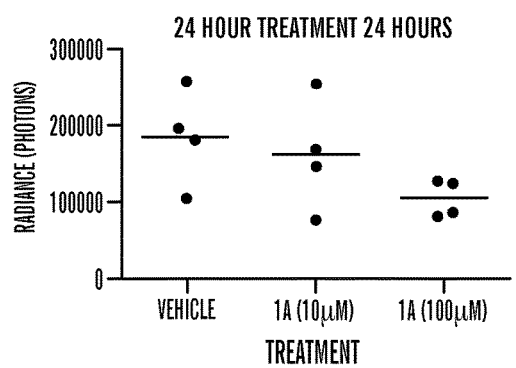
Figure 11F:
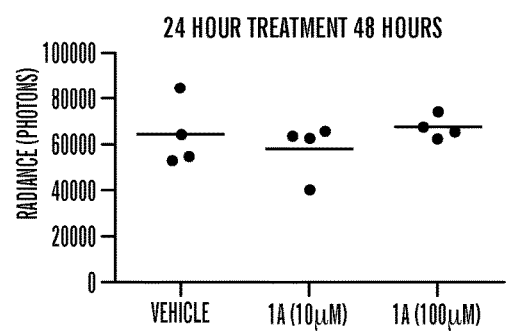
Figure 12D:
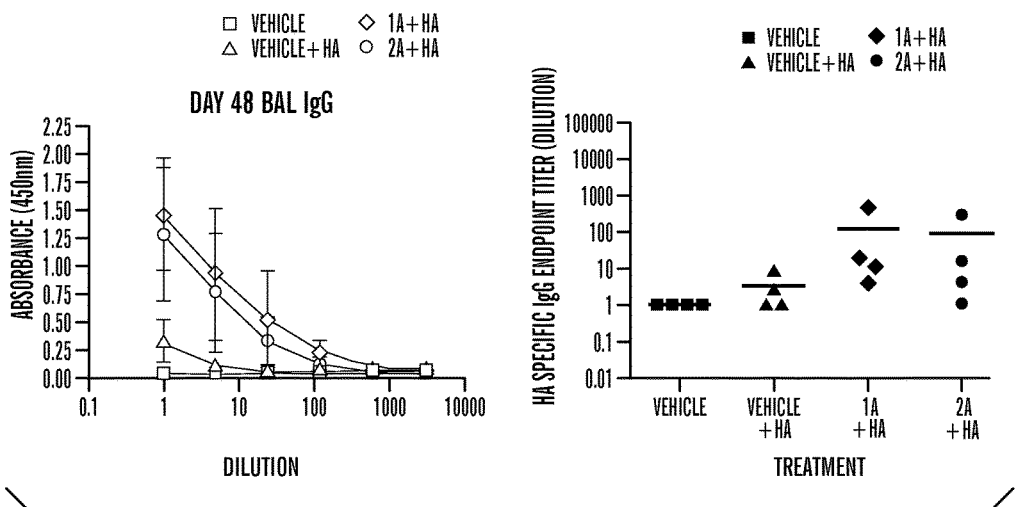
Figure 12E:
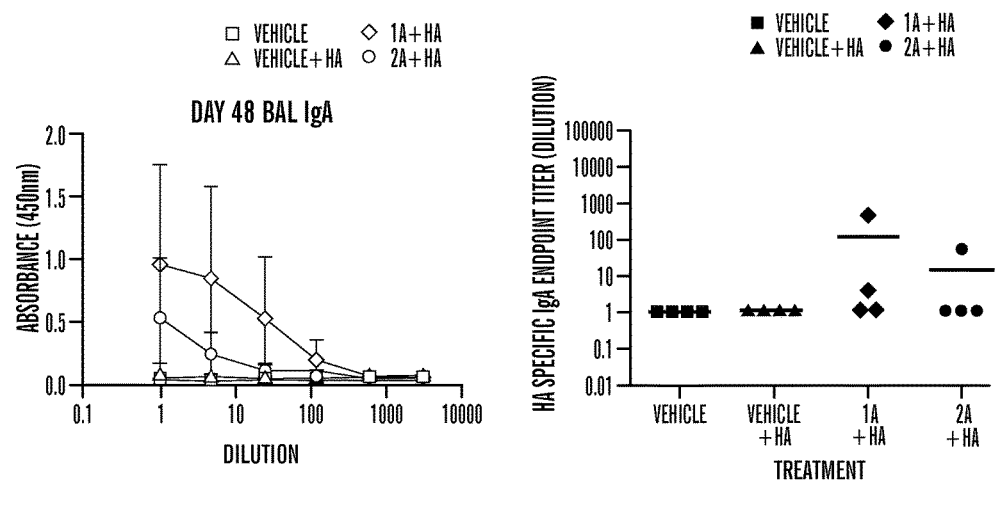

Thioflavin T binding can indicate the presence of the cross-β conformation (Biancalana et al., "Molecular Mechanism of Thioflavin-T Binding to Amyloid Fibrils," *Biochimica et Biophysica Acta* 1804:1405-1412 (2010), which is hereby incorporated by reference in its entirety. Peptide fibrils bound thioflavin T when diluted into either buffer or cell culture media. Both peptides 1a and 2a (already prepared in 0.12% Pluronic® F-127) showed maximum fluorescence immediately upon dilution, so the kinetics of fibril formation could not be determined. Thioflavin T binding was statistically significant (P<0.005) at peptide concentrations as low as 240 nM. 2a fibrils showed an order of magnitude more thioflavin T fluorescence than 1a fibrils, indicating a morphological difference in fibril packing. Considered in full, the results of biophysical characterization of 1a and 2a strongly indicate that these peptide fibrils have a cross-β structure consistent with amyloid. Thioflavin T binding of 1a and 2a is shown in FIGS. 10A-10B.

Figure 5C:
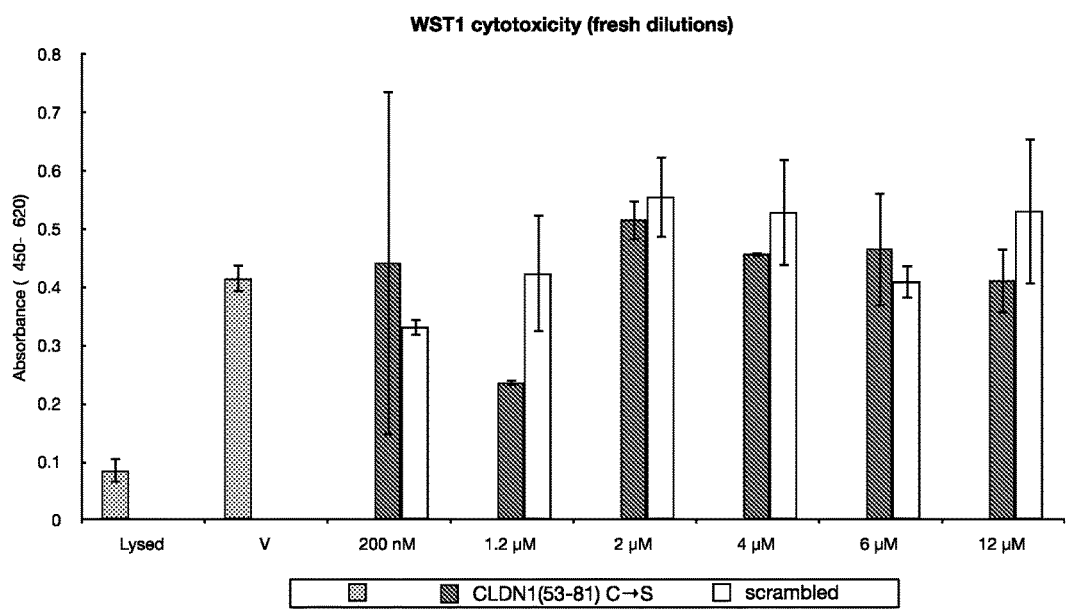

Cytotoxicity associated with amyloid exposure arises from either cytotoxic oligomer formation (Laganowsky et al., "Atomic View of a Toxic Amyloid Small Oligomer," *Science* 335:1228-1231 (2012), which is hereby incorporated by reference in its entirety) or sequestration of essential metastable proteins in the cell (Olzscha et al., "Amyloid-Like Aggregates Sequester Numerous Metastable Proteins with Essential Cellular Functions," *Cell* 144(1):67-78 (2011), which is hereby incorporated by reference in its entirety). Care was taken to limit transient oligomer formation (Cecchi et al., "The Amyloid-Cell Membrane System. The Interplay Between the Biophysical Features of Oligomers/Fibrils and Cell Membrane Defines Amyloid Toxicity," *Biophys. Chem.* 182:30-43 (2013), which is hereby incorporated by reference in its entirety) during cell exposure by allowing peptide self-assembly to reach equilibrium prior to application to cells. This precaution was taken because freshly diluted peptide fibrils induced significant cytotoxicity, consistent with that of other amyloid oligomers (See FIG. 5C) (Doran et al., "Turn Nucleation Perturbs Amyloid β Self-Assembly and Cytotoxicity," *J. Mol. Biol.* 421:315-

328 (2012), which is hereby incorporated by reference in its entirety). These cytotoxic effects (FIGS. 5A-5B) were not observed relative to the vehicle control within the functional concentration range and time course used for peptides 1a and 2a at equilibrium. It was concluded that the functional effects of peptide exposure are not due to necrotic cell death or undue stress on cellular homeostasis.

In amyloid self-assembly, the β-sheet conformation is driven by a combination of backbone and side chain interactions: hydrophobic, aromatic and hydrogen bond formation. In the core of a fibril, side chains at the interface of two β-sheets interdigitate to form a steric zipper (Sawaya et al., "Atomic Structures of Amyloid Cross-β Spines Reveal Varied Steric Zippers," *Nature* 447:453-457 (2007); Nelson et al., "Structure of the Cross-β Spine of Amyloid-Like Fibrils," *Nature* 435:773-778 (2005), which are hereby incorporated by reference in their entirety) running parallel to the fibril axis. Peptides 1a and 2a have 55% polar, uncharged (S, Q, T and N) and 31% hydrophobic residues. Self-assembly of 1a and 2a is likely to be stabilized through side chain hydrogen bonds at this interface. The cross-β conformation is further characterized by a strip of hydrophobic residues running parallel to the fibril axis (Biancalana et al., "Minimalist Design of Water-Soluble Cross-β Architecture," *Proc. Acad. Nat'l. Sci. U.S.A.* 107:3469-3474 (2010), which is hereby incorporated by reference in its entirety). Short segments of amyloid-prone sequence can drive self-assembly (Tsolis et al., "A Consensus Method for the Prediction of 'Aggregation-Prone' Peptides in Globular Proteins," *PLoS ONE* 8:e54175 (2013); Teng et al., "Short Protein Segments Can Drive a Non-Fibrillizing Protein Into the Amyloid State," *Prot. Eng. Des. Sel.* 22:531-536 (2009), which are hereby incorporated by reference in their entirety). PEPFOLD modeling (Thevenet et al., "PEP-FOLD: An Updated De Novo Structure Prediction Server for Both Linear and Disulfide Bonded Cyclic Peptides," *Nucleic Acids Res.* 40:W288-W293 (2012), which is hereby incorporated by reference in its entirety). predicts a β-hairpin structure in the cysteine loop of Cldn1 peptides (residues 53-65), with hydrophobic residues (I and V) aligning at one face of the hairpin, which could drive cross-β packing Retrospective analysis using the AMYLPRED2 method (Tsolis et al., "A Consensus Method for the Prediction of 'Aggregation-Prone' Peptides in Globular Proteins," *PLoS ONE* 8:e54175 (2013), which is hereby incorporated by reference in its entirety) reveals a short segment in Peptide 2a (SEQ ID NO:6), ILTGVST, which is predicted to be amyloid prone. Several other scrambled sequences also showed organogelation in DMSO (See FIG. 1C, as well as CLDN1-BASED palmitoyl-Nyl-GGGMSCVSQSTGQ-IQCK-$NH_2$ (SEQ ID NO:28); palmitoyl-Nyl-GGSCVSQS-$NH_2$ (SEQ ID NO:29); Npg-Nyl-RRGSCVSQSTGQIQCK-GRR-$NH_2$ (SEQ ID NO:30) (Npg=N-(ethylenedioxy)$_2$) ethylaminoglycine); SCRAMBLED Npg-Nyl-RRGISGVQCCQTKQSSGRR) (SEQ ID NO:31). Peptide 2a therefore represents one member of a suite of polar, uncharged sequences that self-assemble into amyloid-like fibrils. Because the scrambled peptide 2a co-localizes with Cldn1 and induces equivalent functional effects to 1a, permeation enhancing activity is not sequence specific. Peptide 2a self-assembles and has the same amino acid content. The data do not indicate whether it is the β-sheet structure of the peptide fibrils itself or the presentation of hydrogen-bond donors/acceptors patterned on an amphipathic cross-β architecture that mediate association with Cldn1 and tight junction disruption. $A\beta_{42}$ alters the barrier function of vascular epithelial cells, inducing a change in Cldn5 localization (Marco et al., "Amyloid Beta-Peptide 1-42 Alters Tight Junction Protein Distribution in Brain Microvessel Endothelial Cells," *Neurosci. Lett.* 401:219-224 (2006), which is hereby incorporated by reference in its entirety). It is an intriguing possibility that amyloid-induced mislocalization of TJ components might offer a general mechanism to disrupt TJ function and this may be relevant for a number of human diseases including Alzheimer's disease. 2.4 µM $A\beta_{42}$ was found to disrupt TJs, but to a lesser extent than peptides 1a and 2a.

The 1a sequence in isolation self-assembles into β-sheet structures in the presence of surfactant. Amyloid-like fibrils represent a thermodynamically favorable folding state for these synthetic peptides, but do not imply amyloid as a native conformation for the intact Cldn1 protein. There is no evidence that claudins or other TJ proteins participate in systemic amyloidosis. However, functional amyloid is found throughout the prokaryotic and eukaryotic kingdoms (Otzen et al., "We Find Them Here, We Find Them There: Functional Bacterial Amyloid," *Cell Mol. Life Sci.* 65:910-927 (2007), which is hereby incorporated by reference in its entirety). For example, the buoyancy organelles of aquatic microorganisms (Bayro et al., "An Amyloid Organelle, Solid-State NMR Evidence for Cross-β Assembly of Gas Vesicles," *J. Biol. Chem.* 287:3479-3484 (2012), which is hereby incorporated by reference in its entirety) are lined with amphipathic amyloid, providing a gas-tight barrier. Cldn1 does spontaneously self-assemble at the cell surface (Sasaki et al., "Dynamic Behavior of Paired Claudin Strands Within Apposing Plasma Membranes," *Proc. Nat'l. Acad. Sci. U.S.A.* 100:3971-3976 (2003), which is hereby incorporated by reference in its entirety), and organization and regulation of TJ are mediated through a complex interplay of protein-protein interactions (Rodgers et al., "Epithelial Barrier Assembly Requires Coordinated Activity of Multiple Domains of the Tight Junction Protein ZO-1," *J. Cell Sci.* 126:1565-1575 (2013), which is hereby incorporated by reference in its entirety). Native Cldn1 could possess significant β-sheet character at the extracellular protein-protein interface, but the challenging problem of determining the structure of full-length and/or membrane-bound Cldn1 will need to be solved in order to address this speculation.

The data demonstrate that these peptides bind to or in close proximity to Cldn1 and appear to alter the cellular trafficking of Cldn1. It is believed that this altered Cldn1 localization causes TJ disruption, and permits molecules as large as antibodies to pass through the barrier in culture. The improved efficacy of structured peptides such as 1a and 2a, relative to previously published results with non-human homologues, demonstrates that its β-sheet conformation can bind Cldn1, although whether binding occurs at the cell surface or during endocytic recycling is unclear. The use of surfactant or membrane for peptide structure could be an advantage. For example, formulation of Cldn1 peptides with therapeutic payloads or vaccine antigens into liposomes or micelle carriers may be carried out as described herein.

Additional exemplary peptides that have shown evidence of self-assembly and are useful in accordance with embodiments illustrated herein are found in FIG. 1C

Example 2

Use of Tight Junction-Disrupting Peptides for Delivery of Luciferase and Vaccine Antigens Luciferase permeability experiments were carried out as follows. Mice (4 mice per group) were treated after anesthetization in the nasal cavity with vehicle alone (0.006% Pluronic F127 in saline) or with varying concentrations of peptide. After 12 or 24 hours, a solution of 10 micrograms luciferase was applied. Mice were then imaged at various time points to determine the amount of luciferase remaining in the nasal cavity. As shown in FIGS. 11A-11F application of peptide 1A resulted in a trend of higher amounts of luciferase lost from the nasal cavity, consistent with a peptide-mediated increase in permeability.

Immunization experiments with influenza hemagglutinin were carried out as follows. Mice (4 mice per group) were treated in the nasal cavity with vehicle alone (0.006% Pluronic F127 in saline), vehicle plus influenza hemagglutinin (HA), or vehicle plus HA plus a permeabilizing agent (peptides 1A or 2A, or semen-derived enhancer of virus infection (SEVI)). Antibody titers to HA in serum were assessed at day 18, 28, and 35 after treatment, and HA-specific IgG and IgA were determined in bronchial lavage at day 48 post treatment. Both serum antibody titers (FIGS. 12A-12C) and HA-specific antibodies in bronchial lavage (FIGS. 12D-12E) show a trend of enhancement in the presence of peptides 1A or 2A, consistent with a peptide-dependent increase in antigen delivery.

Importantly, in each of the luciferase delivery and antigen delivery experiments, no toxicity was observed at the highest dose of peptide tested (100 micromolar).

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed:

1. A transepithelial drug formulation comprising:
a pharmaceutically suitable carrier;
an effective amount of a therapeutic agent; and
an agent that transiently disrupts claudin-1 within tight junctions, wherein the agent comprises one or more peptides including at least 40% polar, uncharged amino acid residues and a self-assembled β-sheet secondary structure, wherein the one or more peptides comprise the amino acid sequence of SEQ ID NO:6.

2. The transepithelial drug formulation according to claim 1, wherein the drug formulation is a transdermal or transmucosal drug formulation.

3. The transepithelial drug formulation according to claim 1, wherein the peptides form one or more fibrils.

4. The transepithelial drug formulation according to claim 1, wherein the amino acid sequence of the one or more peptides comprise at least 50% polar, uncharged amino acid residues.

5. The transepithelial drug formulation according to claim 4, wherein the amino acid sequence of the one or more peptides comprise at least 60% polar, uncharged amino acid residues.

6. The transepithelial drug formulation according to claim 1, wherein the one or more peptides comprise an amino acid sequence of less than 53 amino acid residues.

7. The transepithelial drug formulation according to claim 1, wherein the agent consists of the one or more peptides.

8. The transepithelial drug formulation according to claim 1, wherein the carrier includes a surfactant.

9. A transepithelial vaccine formulation comprising:
a pharmaceutically suitable carrier;
an effective amount of an antigen or antigen-encoding nucleic acid molecule present in the carrier, and optionally one or more adjuvants; and
an agent that transiently disrupts claudin-1 within tight junctions, wherein the agent comprises one or more peptides including at least 40% polar, uncharged amino acid residues and a self-assembled β-sheet secondary structure, wherein the one or more peptides comprise the amino acid sequence of SEQ ID NO:6.

10. A pharmaceutical composition comprising:
an isolated peptide comprising the amino acid sequence SILTGVSTLDQSLKQLSNFSQAVSTQSSR (SEQ ID NO:6) and
a pharmaceutically suitable carrier.

11. The pharmaceutical composition according to claim 10 further comprising:
a therapeutic agent.

12. The transepithelial vaccine formulation according to claim 9, wherein the vaccine formulation is a transdermal or transmucosal vaccine formulation.

13. The transepithelial vaccine formulation according to claim 9, wherein the one or more peptides form one or more fibrils.

14. The transepithelial vaccine formulation according to claim 9, wherein the amino acid sequence of the one or more peptides comprise at least 50% polar, uncharged amino acid residues.

15. The transepithelial vaccine formulation according to claim 14, wherein the amino acid sequence of the one or more peptides comprise at least 60% polar, uncharged amino acid residues.

16. The transepithelial vaccine formulation according to claim 9, wherein the one or more peptides comprise an amino acid sequence of less than 53 amino acid residues.

17. The transepithelial vaccine formulation according to claim 9, wherein the agent consists of the one or more peptides.

18. The transepithelial vaccine formulation according to claim 9, wherein the carrier includes a surfactant.

19. A method of disrupting an epithelial barrier comprising:
applying to an epithelial site an amount of an agent that transiently disrupts claudin-1 within tight junctions that is effective to disrupt claudin-1 in epithelial cells present at the site, wherein the agent comprises a peptide including at least 40% polar, uncharged amino acid residues and a self-assembled β-sheet secondary structure, thereby disrupting barrier formation at the epithelial site, wherein the peptide comprises the amino acid sequence of SEQ ID NO: 6.

* * * * *

UNITED STATES PATENT AND TRADEMARK OFFICE
CERTIFICATE OF CORRECTION

PATENT NO. : 9,757,428 B2  
APPLICATION NO. : 14/912098  
DATED : September 12, 2017  
INVENTOR(S) : Miller et al.

Page 1 of 1

It is certified that error appears in the above-identified patent and that said Letters Patent is hereby corrected as shown below:

In the Specification

Column 1, Lines 10-12, delete "support from the National Institutes of Health under grant number 5 T32 AR007472-25" and insert in its place --government support under AR007472 awarded by the National Institutes of Health--.

Signed and Sealed this  
Twenty-fourth Day of October, 2017

Joseph Matal  
*Performing the Functions and Duties of the*  
*Under Secretary of Commerce for Intellectual Property and*  
*Director of the United States Patent and Trademark Office*